United States Patent
Buersgens et al.

(10) Patent No.: US 12,163,171 B2
(45) Date of Patent: Dec. 10, 2024

(54) METHOD FOR CARRYING OUT A POLYMERASE CHAIN REACTION AND DEVICE FOR CARRYING OUT THE METHOD

(71) Applicant: HP Health Solutions Germany GmbH, Planegg/Martinsried (DE)

(72) Inventors: Federico Buersgens, Planegg/Martinsried (DE); Joachim Stehr, Planegg/Martinsried (DE); Lars Ullerich, Planegg/Martinsried (DE); Lidiya Osinkina, Planegg/Martinsried (DE); Eimantas Ruseckas, Planegg/Martinsried (DE)

(73) Assignee: HP Health Solutions Germany GmbH, Martinsried (DE)

( * ) Notice: Subject to any disclaimer, the term of this patent is extended or adjusted under 35 U.S.C. 154(b) by 399 days.

(21) Appl. No.: 16/343,675

(22) PCT Filed: Oct. 20, 2017

(86) PCT No.: PCT/EP2017/076902
§ 371 (c)(1),
(2) Date: Apr. 19, 2019

(87) PCT Pub. No.: WO2018/073435
PCT Pub. Date: Apr. 26, 2018

(65) Prior Publication Data
US 2020/0063173 A1    Feb. 27, 2020

(30) Foreign Application Priority Data
Oct. 21, 2016   (DE) ..................... 10 2016 120 124.3

(51) Int. Cl.
*C12P 19/34*    (2006.01)
*B01J 19/08*    (2006.01)
(Continued)

(52) U.S. Cl.
CPC ............... *C12P 19/34* (2013.01); *B01J 19/08* (2013.01); *B01L 7/52* (2013.01); *C12Q 1/686* (2013.01);
(Continued)

(58) Field of Classification Search
None
See application file for complete search history.

(56) References Cited

U.S. PATENT DOCUMENTS 5,985,555 A    11/1999   Bertling
6,586,233 B2   7/2003    Benett et al.
(Continued)

FOREIGN PATENT DOCUMENTS

AU    2014280964 A1    4/2015
CN    1477208 A        2/2004
(Continued)

OTHER PUBLICATIONS

MiniPCR, "miniPCR™ mini8 Thermal Cycler User's Guide", 2013-2016, Amplyus LLC, (pp. 1-18).
(Continued)

*Primary Examiner* — Jennifer Wecker
*Assistant Examiner* — Bryan Kilpatrick
(74) *Attorney, Agent, or Firm* — Foley & Lardner LLP

(57) ABSTRACT

A method for amplifying nucleic acids by a polymerase chain reaction in a reaction volume heated using electrical energy. In at least one of the passages of the amplification cycle of the polymerase chain reaction, the ratio of the electrical energy used in the denaturation step to heat the reaction volume to the size of the reaction volume is less than 20 Joule per milliliter. Further shown is a method of amplifying nucleic acids in a reaction volume by using a device that includes a reaction vessel and a heating means with at least one heating element in contact with the reaction
(Continued)

volume where at least one heating element is conjugated to oligonucleotides. Also shown is a device for the amplification of nucleic acids in a reaction volume including a reaction vessel for receiving the reaction volume and a heating means consisting of at least one heating element contacting the reaction volume.

12 Claims, 15 Drawing Sheets

(51) Int. Cl.
  *B01L 7/00* (2006.01)
  *C12Q 1/686* (2018.01)
(52) U.S. Cl.
  CPC .......... *B01L 2300/0627* (2013.01); *B01L 2300/1811* (2013.01); *B01L 2300/1827* (2013.01)

(56) References Cited

U.S. PATENT DOCUMENTS

| | | | |
|---|---|---|---|
| 6,953,659 B2 | 10/2005 | Jacobson et al. | |
| 7,569,366 B2 | 8/2009 | Tsukada | |
| 2003/0094953 A1* | 5/2003 | Brooks | B01L 3/5027 |
| | | | 324/441 |
| 2009/0060795 A1* | 3/2009 | Owen | B01L 7/52 |
| | | | 422/400 |
| 2011/0008797 A1 | 1/2011 | Zilch et al. | |
| 2014/0206412 A1 | 7/2014 | DeJohn et al. | |
| 2014/0377764 A1* | 12/2014 | Stehr | B82Y 20/00 |
| | | | 435/6.12 |
| 2019/0262826 A1 | 8/2019 | Rawle | |

FOREIGN PATENT DOCUMENTS

| | | |
|---|---|---|
| CN | 101889096 A | 11/2010 |
| CN | 104471075 A | 3/2015 |
| CN | 105092543 A | 11/2015 |
| DE | 19543060 A1 | 5/1997 |
| DE | 19960398 B4 | 5/2004 |
| DE | 102013215166 B3 | 10/2014 |
| DE | 102013215168 A1 | 2/2015 |
| EP | 1591543 A2 | 11/2005 |
| EP | 1748084 A1 | 1/2007 |
| EP | 2809806 A1 | 12/2014 |
| WO | WO-02081981 A2 * | 10/2002 ............. F25B 21/04 |
| WO | WO-2002081981 A2 | 10/2002 |
| WO | WO-2007143034 A1 | 12/2007 |
| WO | WO-2014013263 A1 | 1/2014 |
| WO | WO-2014025924 A1 | 2/2014 |
| WO | WO-2016163957 | 10/2016 |

OTHER PUBLICATIONS

Biomeme, "Franklin™ Real-Time PCR Thermocycler and Biomeme Go App" User Manual, 2020, Ver 1.0, (pp. 1-38).
Open PCR, "Open PCR Features", Aug. 19, 2020, (pp. 1-5).
The Ubiquitome, Liberty 16, "Stay Ahead of the Curve", 2020 (pp. 1-2).
Marx V., "PCR heads into the field." Nature Methods. 2015; 12(5): 393-397. doi: 10.1038/nmeth.3369.
Duwensee, Flechsig et al. "Electrochemical product detection of an asymmetric convective polymerase chain reaction", Biosensors and Bioelectronics, (2009) (p. 400-405).
Mirallas et al. "A Review of Heating Temperature Control in Microfluidic Systems", Diagnostics (2013) (pp. 33-67).
Reske, Flechsig et al. "Electrochemical detection of osmium tetroxide-labeled PCR-products by means of protective strands", Science Direct (2007) (pp. 393-397).
Hu, Guoqing, et al., "Electrokinetically controlled real-time polymerase chain reaction in microchannel using Joule heating effect", Nov. 8, 2005, Analytica Chimica Acta 557 (2006) pp. 146-151.
Grace Wong et al: "A Rapid and Low-Cost PCR Thermal Cycler for Low Resource Settings", PLOS One, vol. 10, No. 7, Jul. 6, 2015, pp. 1-20.
Neuzil P et al: "Ultra fast miniaturized real-time PCR: 40 cycles in less than six minutes", Nucleic Acids Research, Oxford University Press, GB, vol. 3-14, Jun. 28, 2006 pp. 1-9.

* cited by examiner

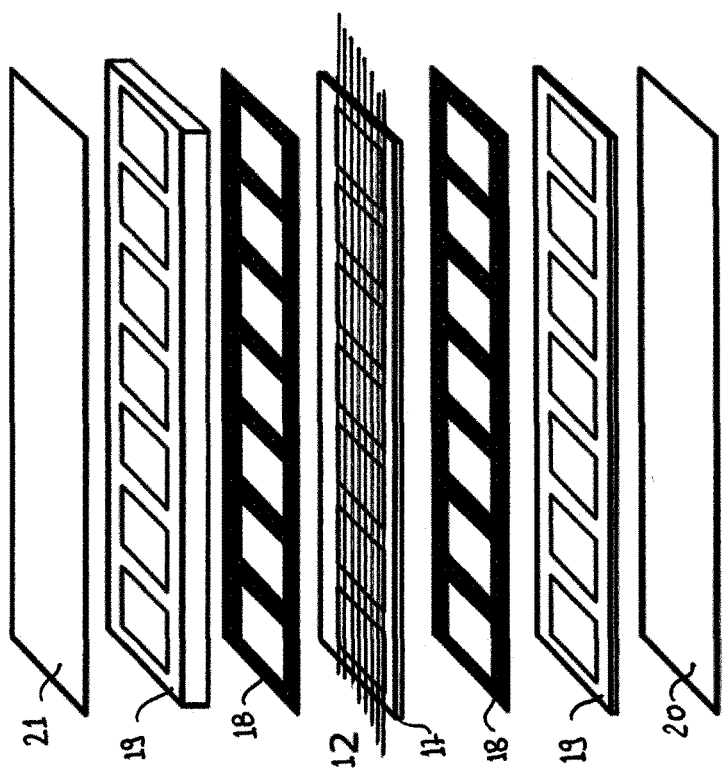
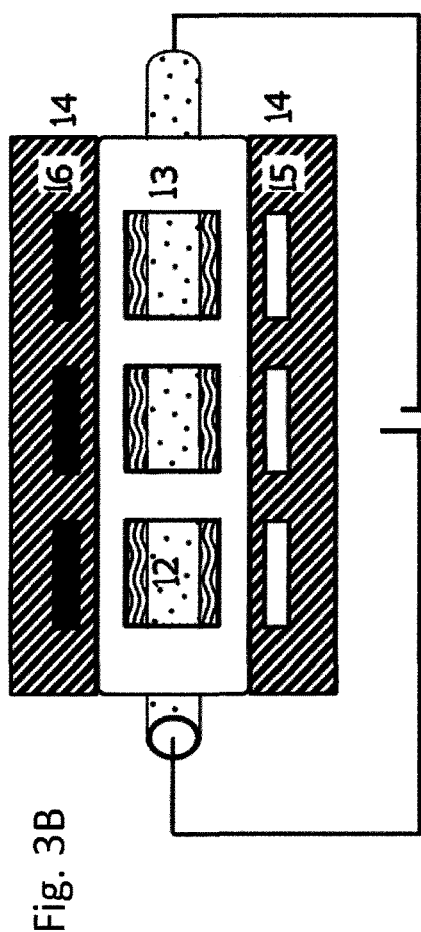
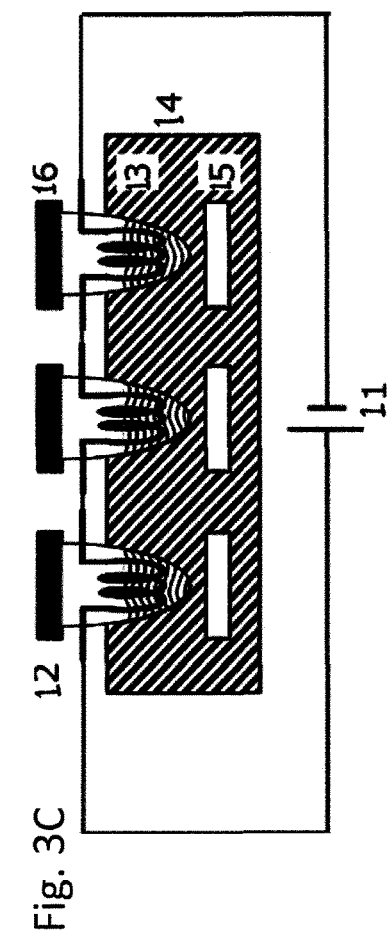
Fig. 3B
Fig. 3C
Fig. 3D

METHOD FOR CARRYING OUT A POLYMERASE CHAIN REACTION AND DEVICE FOR CARRYING OUT THE METHOD

CROSS REFERENCE TO RELATED APPLICATIONS

This application is a national stage application under 35 U.S.C. § 371 of PCT Application No. PCT/EP2017/076902, filed Oct. 20, 2017, which claims priority to and the benefit of German Patent Application No. 10 2016 120 124.3 filed Oct. 21, 2016, which are incorporated herein by reference in their entirety. This application specifically incorporates by reference the sequence listings filed with PCT Application No. PCT/EP2017/076902, which listings were incorporated by reference in that application.

FIELD OF THE INVENTION

The invention relates to a method for the amplification of nucleic acids in a reaction volume which is heated. It further relates to a use of a device which has a reaction vessel for receiving the reaction volume and a heating means for the amplification of nucleic acids. Finally the invention relates to a device for the amplification of nucleic acids in a reaction volume, which has a reaction vessel for receiving the reaction volume and a heating means.

BACKGROUND OF THE INVENTION

U.S. Pat. No. 7,569,366 B1 discloses a method for the amplification of nucleic acids by means of a polymerase chain reaction (PCR), wherein a reaction vessel is arranged on a heating block in order to pre-heat it to an annealing temperature. The reaction vessel is equipped with a heating means in the form of a resistance wire coil or a thin film, which is in direct contact with the reaction volume in the reaction vessel in order to heat this temporarily to an elongation temperature and a denaturation temperature. For this purpose, an electrical current pulse is supplied to the heating means. The pulse duration is to be in the order of at least milliseconds, the denaturation time at least around ten milliseconds. In an exemplary embodiment the pulse duration is 100 mm (milliseconds) and the volume of the reaction vessel is 200 μl (microlitres).

U.S. Pat. No. 6,586,233 B2 discloses a system for carrying out a PCR, which has a chamber with an upper temperature zone and a lower temperature zone, as well as ducts which connect the upper and the lower temperature zone to each other. By means of convective pumping, a sample liquid is repeatedly guided through the upper and lower temperature zones in order to achieve a temperature change.

In the international application laid open for public inspection WO 2007/143034 A1, a method is disclosed that is to be suitable for performing a PCR, and with which the temperature change is to be optically induced. It is proposed for example to irradiate nanoparticles with femto-second pulses of a titanium-sapphire laser or nanoparticles or a gold film with an argon-ion laser.

The European application laid open for public inspection EP 2809806 A1 discloses a method for the amplification of nucleic acids by means of a PCR on nanoparticles in a reaction volume, which are excited by a laser for the emission of heat. The nanoparticles are conjugated to primers of the PCR.

In the German application laid open for public inspection DE 19543060 A1, a method is disclosed, which is to be suited for carrying out electrochemical measurements on a directly heated, wire-form electrode at temperatures above the boiling point of an electrolyte solution. For this, the sample is heated with short-term, intensive alternating current pulses to high temperatures that lie above the boiling point of the electrolyte solution, while the temperature of the remaining solution is virtually unaffected. Then, the local excess temperature rapidly drops, whereby a boiling of the electrolyte solution and other interference-causing effects are to be avoided.

The German application laid open for public inspection DE 199600398 B4 discloses a method which is to be suited for biochemical analysis and wherein an electrode of an electrochemical sensor is modified at its surface with nucleic acid molecules or fractions thereof, which serve as probe sequences for the detection of target sequences. The sensor is heated directly by means of alternating current, wherein merely a very thin layer of a solution under examination close to the electrode surface is heated, but most of the solution remains at virtually unchanged temperature.

Reske, Flechsig et al. report, in "Electrochemical detection of osmium tetroxide-labelled PCR-products by means of protective strands", Talanta 74 (2007), pages 393 to 397, on a method for the electrochemical detection of products of polymerase chain reactions. Here, firstly a conventional PCR is carried out in order to amplify the DNA to be detected. Then the amplified DNA double strands are separated off and marked with electrochemically active osmium tetroxide bipyridine. These were brought into contact with a gold electrode, on which DNA-probe strands were immobilised. Through voltammetric measurements, the authors seek to have detected a hybridisation of the marked strands to the probe stands.

Duwensee, Flechsig et al. report, in "Electrochemical product detection of an asymmetric convective polymerase chain reaction"; Biosensors and Bioelectronics 25 (2009), pages 400 to 405, on a method for carrying out a PCR by means of convention convection. For this, a platinum wire was guided through the lower area of a sample tube and was heated to an estimated temperature of 89° C. by supplying a heat current for the duration of the experiments of up to 45 minutes. In addition the sample tube was placed in a water bath with a temperature of 50° C. The authors report that, in the reaction volume, convection with two (eddy) swirls, with central axes running parallel to the heating wire, came about.

Object of the Invention

It is the object of the invention to provide an improved method for the amplification of nucleic acids in a reaction volume, which is heated. It is also the object of the invention to provide a new use of a device having a reaction vessel for receiving the reaction volume and a heating means. Finally, it is the object of the invention to provide an improved device for the amplification of nucleic acids in a reaction volume having a reaction vessel for receiving the reaction volume and a heating means.

Solution According to the Invention

In one aspect of the invention the object thereof is accomplished through a method for the amplification of nucleic acids by means of a PCR in a reaction volume, wherein the reaction volume is heated using electrical energy, wherein, in at least one of the passages of the amplification cycle of the PCR, the ratio of the electrical energy used in the denaturation step to heat the reaction volume to the value of the reaction volume is less than 20 Joule per mL (millilitre).

A PCR in the sense of the present invention is a method for the amplification of nucleic acids, wherein an amplification cycle consisting of the steps of denaturation, hybridisation and elongation is repeatedly passed through, and indeed preferably in this sequence. In each passage of the cycle the number of nucleic acid molecules can be increased (typically doubled in the best case scenario), so that an exponential increase in the number of nucleic acid molecules can arise. A nucleic acid to be amplified is referred to below as an "original". The original is a single strand and can form, together with its complementary strand, which is referred to as a "complement", a double strand. The original and also the complement can be part of a larger nucleic acid. In particular in a PCR, a copy of the original produced in one passage of the amplification cycle can form a template for the formation of a complement in a subsequent passage and a copy of the complement produced can be a template for the formation of an original in a subsequent passage of the cycle. A common term for the amplification product is "amplicon".

The denaturation step serves to denature a nucleic acid double strand, i.e. to separate it into its two single strands. In the denaturation step, for example, the original can be separated from the complement. The type of denaturation that is preferred according to the invention is thermal denaturation (also referred to as "melting"). For this, at least a part of the nucleic acid double strand or the entire double strand is exposed to a temperature, described as the "denaturation temperature", which brings about or at least encourages a separation of the nucleic acid double strands. The preferred denaturation temperature is selected on the one hand to be so high that nucleic acid double strands can be separated. On the other hand the preferred denaturation temperature is selected to be so low that a DNA polymerase, which is possibly also present in the sample, is not significantly damaged. A typical value for the denaturation temperature is 95° C.

To facilitate the following explanation of the invention, "denaturation step" is used in the terminology of the present invention to describe the step of the method, in which the heating means produces heat in order to heat the reaction volume and to bring about a denaturation of double-stranded nucleic acid molecules in this way. The duration of the denaturation step is accordingly the sum of the time, in which the heating means produces heat in the passage of the cycle of the PCR relating to the denaturation step. In the case of a heating resistor being used as a heating means, the duration of the denaturation step, thus the duration of a transmission of electricity by the heating means in order to heat the reaction volume and to bring about a denaturation of double-stranded nucleic acid molecules in this way. If the heating means in a passage of the amplification cycle produces the heat not in one but in a plurality of time intervals separated from each other (which can be advantageous, as will be explained below), the duration of the denaturation step is the sum of the durations of these intervals. In the denaturation step defined in this way, in particular the emission of heat based on the heat capacity of the heating means itself is not included and nor is the subsiding of the temperature in the part of the reaction volume adjacent to heating means, even if the temperatures present there are still within the range required for denaturation. This means in particular that, in the method according to the invention, denaturation can also still take place after the thus defined denaturation step. It also means that heat emitted in the denaturation step is generally less than the heat generated in the denaturation step.

Furthermore the PCR preferably uses at least two oligonucleotides, which are described as "primers": a forward primer and a reverse primer. The forward primer is complementary to the 3'-end of the original and the reverse primer is complementary to the 3'-end of the complement. In the hybridisation step (also referred to as the "annealing step"), the forward primer and/or the reverse primer hybridise(s) to a sequence complementary thereto in the original or complement or amplicon. The hybridisation step usually takes place at a temperature that brings about or at least encourages a hybridisation of the forward and reverse primers to their complementary sequences in the original or complement or amplicon. It is preferably selected so that it facilitates a hybridisation of the primers that is as specific as possible. The hybridisation temperature is typically between 50° C. and 72° C.

In the elongation step, the hybridised primers are complementarily elongated by a polymerase enzyme. Thus, starting from the forward primer, a complement and, starting from the reverse primer, an original can be synthesised. For the purpose of elongation the polymerase is exposed to a temperature that facilitates or at least encourages an elongation. When using a polymerase of *Thermus aquaticus* (Taq), an elongation temperature of 72° C. is typically used. In some embodiments of the PCR the hybridisation and the elongation temperatures are identical, i.e. both steps take place at the same temperature. (This means that there are only two temperature levels during the PCR, a combined hybridisation and elongation temperature and a denaturation temperature.)

The terms "nucleic acid" and "oligonucleotide" include in the context of the present invention not only (desoxy)-ribonucleic acids and (desoxy)-oligoribonucleotides, even if the aforesaid are preferred, but also nucleic acids and oligonucleotides that contain one or more nucleotide analogues with modifications on their backbone (e.g. methylphosphonates, phosphorothioates or peptic nucleic acids (PNA), in particular on a sugar of the backbone (e.g. 2'-O-alkyl derivatives, 3'- and/or 5'-aminoriboses, locked nucleic acids (LNA), hexitol nucleic acids, morpholinos, glycol nucleic acid (GNA), threose nucleic acid (TNA) or tricyclo-DNA—see in this connection the dissertation by D. Renneberg and C. J. Leumann, "Watson-Crick base-pairing properties of Tricyclo-DNA", J. Am. Chem. Soc., 2002, Volume 124, pages 5993-6002, of which the related content is to be regarded as part of the present disclosure by virtue of reference thereto) or that contain base analogues, e.g. 7-deazapurine or universal bases such as nitroindole or modified natural bases such as N4-ethyl-cytosine. In one embodiment of the invention the nucleic acids or oligonucleotides are conjugates or chimera with non-nucleoside analogues, e.g. PNA. In one embodiment of the invention, the nucleic acids or oligonucleotides contain, at one or more positions, non-nucleoside units such as spacers, e.g. hexaethylene glycol or Cn-spacers with n between 3 and 6. If the nucleic acids or oligonucleotides contain modifications these are selected so that, also with the modification, hybridisation with natural DNA/RNA analytes is possible. Preferred modifications influence the melt behaviour, preferably the melt temperature, in particular in order to be able to differentiate hybrids with different degrees of complementarity of their bases (mismatch discrimination). Preferred modifications include LNA, 8-aza-7-deazapurine, 5-propinyl-uracil and cytosine and/or abasic interruptions or modifications in the nucleic acid or in the oligonucleotide. Further modifications in the sense of the invention are, e.g., modifications with biotin, thiol and fluorescence donor and fluorescence acceptor molecules.

The method according to the invention takes place in a reaction volume. This means in the sense of the present invention that the amplification of the nucleic acids takes place at least in a part of the cohesive reaction volume. The reaction volume is a liquid solution or suspension, which, besides the solvent or suspension medium, preferably water, usually also contains the nucleic acid(s) to be amplified ("target nucleic acid(s)" is also used below). It generally also contains originals and complements and/or other constituent parts, for example polymerase(s), dNTPs and salts, which can be suspended or dissolved.

In the sense of the present invention the "electrical energy used for heating" is the energy that is used directly or indirectly to heat the reaction volume. According to this definition it is generally different from the heat supplied to the reaction volume. This difference can hardly be seen or cannot be seen at all for example when using a heating resistor as a heating means, because in this case the electrical energy used for heating is almost completely converted into heat in the heating resistor through the current flow in such a way that with a suitable arrangement of the heating resistor, the electrical energy used for heating can be supplied almost completely to the reaction volume. However, the difference is highly perceivable for example in the case of the method known from EP 2809806 A1, wherein nanoparticles are excited with a laser for heat emission, because the electrical energy used for heating in this case is the electrical energy with which the laser is operated, and this does not heat the reaction volume until on the detour via the laser and the nanoparticles. Due to the low degree of efficiency of the detour via the laser and the nanoparticles, only a small part of the electrical energy used for the heating is actually supplied as heat to the reaction volume.

Where reference is made in connection with the present invention to "heating the reaction volume", this does not necessarily mean in the sense of the invention that the whole reaction volume has to be heated, let alone having to be heated evenly. Instead, non-homogeneous heating or heating only of parts of the reaction volume is also regarded as heating of the reaction volume in the sense of this invention.

In a further aspect of the invention the object of the invention is accomplished by a method for the amplification of nucleic acids by means of a PCR in a reaction volume, wherein a heating means consisting of one or a plurality of electrically contacting heating elements, which are in contact with the reaction volume, heats the reaction volume, wherein. in at least one of the passages of the amplification cycle of the PCR, the heating means supplies less heat generated in the denaturation step to the reaction volume than $C_R*5°$ C. (degrees Celsius). $C_R$ is the heat capacity of the reaction volume during the heating by the heating means (both here, and also below, the heat capacity of a body is indicated by the capital letter "C", but the specific heat capacity with by small letter "c"). In other words, without considering other heat inflows and outflows, the heating means heats the reaction volume by on average less than 5° C.

In a further aspect of the invention the object of the invention is accomplished by a method for the amplification of nucleic acids by means of a PCR in a reaction volume, wherein a heating means, which is in contact with the reaction volume, heats the reaction volume, wherein, in at least one of the passages of the amplification cycle of the PCR, the maximum increase of the average temperature taking place through the denaturation step (hereinafter also referred to as "MGTE" of the reaction volume is less than 10° C.

The heating means in the sense of the present invention is thus the sum of the heating elements. In the sense of the present invention "contact" means, with respect to heating elements and reaction volume, that the reaction volume is adjacent to an area of the heating element. If the heating element comprises a material (hereinafter also referred to as a "separating layer"), which is arranged between the heat-generating component of the heating element and the reaction volume, "contact" means that the heating element is in contact, via a face of this separating layer facing towards the reaction volume, with the reaction volume. It is an achievable advantage of this contact between the heating element and reaction volume that the reaction volume can be heated by the heating element in the vicinity of the heating element.

In a further aspect of the invention the object of the invention is achieved by a method for the amplification of nucleic acids by means of a PCR in a reaction volume, wherein a heating means consisting of one or more heating elements, which are in contact with the reaction volume, heats the reaction volume, wherein, in at least one of the passages of the amplification cycle of the PCR, the heating means supplies less heat generated in the denaturation step to the reaction volume than $C_R*5°$ C., and wherein $C_R$ is the heat capacity of the reaction volume during the heating through the heating means, and that no temporally stable temperature gradient is established, during the whole denaturation step, on at least 10% of the contact area of the heating means with the reaction volume.

A temperature gradient is deemed, at a point in time $t_1$ after the start $t_0$ of the heating by the heating element, to be "temporally stable" in the sense of the present invention if the amount of its maximum incline at a time $t_2=t_0+2*(t_1-t_0)$ has changed by less than 20% with respect to the amount of its maximum incline at the point in time $t_1$. In order to ascertain the temporal stability, it is merely the comparison of the amounts of the maximum gradient that is relevant, but not whether or not the heating means generates heat at the point in time $t_2$. Preferably, the amount of the gradient at the point in time $t_2$ has changed by less than 10%, particularly preferably by less than 5%, particularly preferably by less than 3%, particularly preferably by less than 1%. The gradient generally has its maximum incline at the surface of the heating means.

In a further aspect of the invention the object of the invention is achieved by the use of a device comprising a reaction vessel for receiving the reaction volume and a heating means consisting of one or more heating elements, which are in contact with the reaction volume in order to heat it, for the amplification of nucleic acids in a reaction volume, wherein at least one of the heating elements is conjugated to oligonucleotides.

In a further aspect of the invention the object of the invention is achieved by a device for the amplification of nucleic acids in a reaction volume comprising a heating means consisting of one or more heating elements, which can be in contact with the reaction volume, in order to heat it.

In a further aspect of the invention the object of the invention is achieved by a device for the amplification of nucleic acids in a reaction volume, which comprises a heating means consisting of one or more heating elements to heat the reaction volume using electrical energy and a means for bringing the electrical energy into the device, wherein the device is designed so that its electrical power consumption does not exceed 50 W (Watt) at any point in time.

In a further aspect of the invention the object of the invention is achieved by a device for the amplification of nucleic acids in a reaction volume, which comprises a reaction vessel for receiving the reaction volume, a heating means consisting of one or more heating elements to heat the reaction volume using electrical energy and a means for bringing the electrical energy into the device, wherein the device is designed so that the ratio between the electrical power consumption and the capacity of the reaction vessel does not exceed 1 W/ml (Watt per millilitre) at any point in time during the PCR. This restriction does not apply to possibly higher power consumptions during the switch-on process of the device that may be caused by technically based starting currents. Such increased power consumptions are not regarded as power consumptions during the PCR, and are not therefore considered here.

In a further aspect of the invention the object of the invention is achieved by a device for the amplification of nucleic acids in a reaction volume by means of a PCR, which comprises a reaction vessel for receiving the reaction volume, a heating means consisting of one or more heating resistors, and a control device, which applies electrical current to the heating means in order to heat the reaction volume, wherein the control device is designed so that, in at least one of the passages of the amplification cycle of the PCR, the ratio between the electrical energy applied to the heating element by the control device in the denaturation step, and the capacity of the reaction vessel is less than 40 J/mL (Joules per milliliter).

In a further aspect of the invention the object of the invention is achieved by a device for the amplification of nucleic acids in a reaction volume by means of a PCR, which comprises a reaction vessel for the reaction volume, a heating means consisting of at least one heating element, in order to heat the reaction volume, and a control device in order to control the heat emission of the heating means to the reaction volume, wherein the control device is designed so that, in at least one of the passages of the amplification cycle of the PCR, the ratio between the amount of heat emitted by the heating means in the denaturation step to the reaction volume, and the capacity of the reaction vessel for receiving the reaction volume, is less than 20 J/mL, and at least one heating element of the heating means has an expansion of more than 1.5 μm (micrometres) in at least one direction.

The invention is based, inter alia, on the recognition by the inventors that, in known amplification methods, the duration of thermalisation required for the temperatures of the reaction volume that need to be established for the different steps of the nucleic acid amplification makes a considerable contribution to the method duration and that the method duration could be shortened by shortening these phases. It is further based on the recognition by the inventors that the method can also be carried out efficiently when one or more temperature(s) required for the PCR are only achieved in a part of the reaction volume. The invention is also based on the recognition that this can be achieved with significantly lower energy use than in the prior art.

In particular it can be achieved with the invention that— for example with the aid of short electrical impulses—only the direct vicinity of the heating element(s) of the heating means is heated for a short time, preferably in order to carry out the denaturation of the nucleic acid molecules in the reaction volume, while the majority of the reaction volume remains at a (in this sense "global") base temperature, at which in particular an elongation, preferably also a hybridisation, can take place. This is preferably achieved by the duration of the heating through the heating means being so short that the thermal field arising in the surrounding reaction volume can only spread a few micrometres and in this way creates a heating-up zone, which preferably comprises only a tiny fraction of the reaction volume. In particular the amount of heat brought can be so low that no substantial global heating of the reaction volume takes place.

The "global temperature" in the sense of the present invention is the average temperature, with respect to volume, of the reaction volume, thus the temperature that is established or would be established in the reaction volume after a thermalisation thereof. The "global heating" is the increase in the global temperature defined in this way.

Furthermore it can be achieved with the invention that, after heating, in particular in the denaturation step, the heat brought, which spreads from the heating-up zone into the rest of the reaction volume, only brings about a negligible global temperature increase there. "Negligible" means here in particular that the temperature increase is preferably too low for a denaturation of the nucleic acid molecules and particularly preferably that the temperature increase is too low to interfere with the hybridisation and the elongation.

The denaturation and preferably also other steps of the nucleic acid amplification can thus take place locally in the direct vicinity of the heating elements, wherein at least one of the required primers is fixed (hereinafter referred to as: "functionalised") on the heating means, in order to allow the amplicon also to form there and thus to facilitate a denaturation with local heating. In other words, due to the fact that, based on the functionalisation of the heating means, a localisation of steps of the PCR, in particular hybridisation, elongation and/or denaturation, as well as preferably also the generation of a signal to observe the progress of the PCR, is achieved in the direct vicinity of the heating means, the heating of the reaction volume can be limited to a fraction of the reaction volume.

It is achievable with the invention that nucleic acids can be amplified more rapidly. In particular, in contrast with conventional thermocyclers, in which the heating and cooling processes last many seconds, it can be achieved with the invention that the duration of the PCR is no longer determined by technical limitations such as the heating and cooling rates. Thermalisation times in the reaction vessel can also be omitted, as the heat is constantly generated in the vicinity of the heating means. The inventors ascertained that, even in the case of 40 passages of the amplification cycle of a PCR, the denaturation of the nucleic acid molecules and the cooling thereof to an elongation and hybridisation temperature, only take a few milliseconds in total. It can be achieved through the invention that the duration of the PCR is determined predominantly by the durations between the denaturation steps that are required for the diffusion and reaction processes and the biochemical processes such as elongation by the polymerase.

It is also achievable with the invention that nucleic acids can be amplified with lower energy use. Furthermore the invention enables the amplification process to be controlled more effectively and for example to extensively avoid the temperature fluctuations of the reaction volume that arise within the temperature control in the known methods. More cost-effective and more compact device for the amplification of nucleic acids can be provided by the invention. For example it can be achieved to provide a device according to the invention for the amplification of nucleic acids in the form of a universal serial bus (USB) stick.

Preferred Embodiments of the Invention

Advantageous embodiments and refinements, which can be used individually or in combination with each other, are the subject matter of the dependent claims.

In a preferred embodiment of the invention, in at least one, preferably in at least three, particularly preferably in at least 10, particularly preferably in at least 20, of the passages of the amplification cycle of the PCR, the ratio of the electrical energy used in the denaturation step for heating the reaction volume to the size of the reaction volume is less than 20 J/mL, preferably less than 10 J/mL. With this embodiment of the invention a low energy consumption of the method according to the invention can advantageously be achieved. In addition, the addition of energy in the denaturation step being so great that it leads to an excessive global heating of the reaction volume can be advantageously avoided.

In a preferred embodiment of the invention, in at least one, preferably in at least three, particularly preferably in at least 10, particularly preferably in at least 20, of the passages of the amplification cycle of the PCR, the ratio of the electrical energy used in the denaturation step for heating the reaction volume to the size of the reaction volume is between 0.01 and 30 W/mL (Watt per millilitre), preferably between 0.05 and 10 W/ml, and particularly preferably between 0.1 W and 5 W/mL.

In one embodiment of the invention the denaturation step comprises a plurality of time intervals spaced apart from each other, in which the heating means produces heat in the passage of the cycle of the PCR relating to the denaturation step. In each case the time-based distance of the time intervals of the current pulses must be very much smaller than the sample thermalisation time; particularly preferably the time-based distance of the time intervals of the current pulses must be selected so that the temperature of the heating means between the time intervals decreases less than 20%. This embodiment of the invention can be favourable for example if a switching power supply is used for energy supply. Particularly preferably the denaturation step is realised through a current impulse or a plurality of current impulses, wherein the absolute amount of the current strength during the time duration or the current impulse(s) in a preferred embodiment varies by less than 10%. In this way, smooth dynamics of the heating of the reaction volume can be achieved.

In a preferred embodiment of the invention in at least one, preferably in at least three, particularly preferably in at least 10, particularly preferably in at least 20, of the passages of the amplification cycle of the PCR, the ratio of the electrical energy used in the denaturation step for heating the reaction volume to the size of the reaction volume is greater than 10 mJ/mL (millijoules per millilitre), preferably greater than 30 mJ/mL and particularly preferably greater than 100 mJ/mL. The energy is calculated in one embodiment with constant electrical power used simply from the product of this used electrical power and the duration of the denaturation step. It is an achievable advantage of this embodiment of the invention that the energy is sufficiently great In order to operate a heating means with an area in contact with the reaction volume, of which the size is sufficient in order to meet the requirements that are common in practice for the reaction kinetics of the PCR.

Preferably in at least one, particularly preferably in at least three, particularly preferably in at least 10, particularly preferably in at least 20, of the passages of the amplification cycle of the PCR, the heating means supplies to the reaction volume less heat generated in the denaturation step than $C_R * 5°$ C. (Celsius). $C_R$ is hereby the heat capacity of the reaction volume during the heating by the heating means. In other words, if other heat inflows and outflows are left out of consideration, the heating means heats the reaction volume by on average less than 5° C.

Preferably in at least one, particularly preferably in at least three, particularly preferably in at least 10, particularly preferably in at least 20, of the passages of the amplification cycle of the PCR, the maximum MGTE of the reaction volume is less than 10° C., particularly preferably less than 7° C., particularly preferably less than 5° C., particularly preferably less than 4° C., particularly preferably less than 3° C., particularly preferably less than 2° C., particularly preferably less than 1° C., particularly preferably less than 0.75° C., particularly preferably less than 0.5° C. and most particularly preferably less than 0.3° C.

Values for the MGTE of 4° C. and more can be advantageous in particular if the combined hybridisation and elongation temperature increases in the course of the PCR (for example because the local amplicon density on the heating element greatly increases in the course of the PCR), i.e. in order to also (slightly) change the global temperature via the local heating. In addition, in this way the heat power provided externally, for example by a temperature-regulating block can be reduced, which can further reduce the total power requirement of a device according to the invention. Low values for the MGTE can be advantageous in order to be able to carry out passages of the amplification cycle of the PCR one after the other in very quick succession, or, in order to be able to thermally insulate the sample well with respect to the vicinity and thus make it independent of ambient conditions. If for example the combined hybridisation and elongation temperature is 70° C. and the volumetrically averaged temperature of the reaction volumes after a denaturation step increases to 70.6° C., then the MGTE=0.6° C. here.

In a preferred embodiment of the invention, in at least one, preferably in at least three, particularly preferably in at least 10, particularly preferably in at least 20, of the passages of the amplification cycle of the PCR, during the denaturation step no temporally stable temperature gradient is established on at least 10%, preferably at least 30%, particularly preferably at least 50%, particularly preferably at least 80%, of the contact surface of the heating means with the reaction volume.

In a preferred embodiment of the invention in at least one, preferably in at least three, particularly preferably in at least 10, particularly preferably in at least 20 of the passages of the amplification cycle of the PCR, for at least half the duration of the denaturation step, the maximum incline of the temperature gradient is greater than 0.5° C./μm, particularly preferably greater than 1° C./μm, and most particularly preferably greater than 3° C./μm. An achievable advantage of this embodiment of the invention is achieving a good localisation of the temperature increase brought about by the heating element, as a localisation of the temperature increase necessarily requires the formation of a gradient (the temperature gradient does not therefore have to be temporally constant in this embodiment).

In a preferred embodiment of the invention in at least one, preferably in at least three, particularly preferably in at least 10, particularly preferably in at least 20 of the passages of the amplification cycle of the PCR, for at least half the duration of the denaturation step, the maximum incline of the temperature gradient is less than 1000° C./μm, particularly preferably less than 300° C./μm. It is an achievable advantage of this embodiment of the invention that thermophoretic effects in the solution can be avoided.

In a preferred embodiment of the invention in at least one, preferably in at least three, particularly preferably in at least 10, particularly preferably in at least 20 of the passages of the amplification cycle of the PCR, the cycle duration $t_c$ is shorter than 60 s (seconds), preferably shorter than 40 s, particularly preferably shorter than 20 s, particularly preferably shorter than 15 s, particularly preferably shorter than 10 s. In the sense of the present invention the cycle duration $t_c$ is the duration of a passage of the amplification cycle of the polymerase chain reaction consisting of the steps of denaturation, hybridisation and elongation in this sequence. By selecting a particularly short cycle duration $t_0$, a particularly rapid PCR method can be realised in this embodiment of the invention.

In a preferred embodiment of the invention in at least one, preferably in at least three, particularly preferably in at least 10, particularly preferably in at least 20 of the passages of the amplification cycle of the PCR, the duration of the PCR $t_{PCR}$ is shorter than 45 minutes, particularly preferably shorter than 30 minutes, particularly preferably shorter than 20 minutes, particularly preferably shorter than 15 minutes and particularly preferably shorter than 10 minutes. The duration is the time from the start to the end of the PCR, wherein the start of the PCR is the point in time of the start of the denaturation step of the first complete passage of an amplification cycle consisting of the steps of denaturation, hybridisation and elongation in this sequence, and the time of the end of the PCR is the end of the denaturation step of the last complete passage of the amplification cycle with the steps of denaturation, hybridisation and elongation in this sequence.

Heating Means

In a preferred embodiment of the invention the reaction volume is heated by a heating means made up of one or more heating elements, wherein particularly preferably the heating element or at least one of the heating elements, particularly preferably all heating elements, are in electrical contact. It can advantageously be achieved in this way that current can flow through the heating element. This embodiment of the invention can utilise the fact that electrically contact heating elements can be operated and regulated particularly simply by an electrical control device.

The heating element, or one of the heating elements, is preferably a device that converts a current flow into heat, for example through its ohmic resistance. This embodiment of the invention can exploit the fact that such heating elements can convert electrical energy efficiently into heat. A preferred heating element is a heating resistor or a Peltier element. In the case of a plurality of heating elements, these can be arranged in series or in parallel, or partially in series and partially in parallel.

Preferred heating elements can have a material which is arranged between the heat-generating component of the heating element and the reaction volume. Such a material can be useful in order to protect the heating element for example from corrosion or other chemical interactions with the PCR chemistry and/or to electrically insulate it (it is thus described here as a "separating layer") and can consist for example of polymers. Preferably such heating elements and the reaction volume are maximally separated by a separating layer of a thickness of less than 500 µm, preferably a thickness of less than 100 µm, preferably a thickness of less than 20 µm, preferably a thickness of less than 5 µm, preferably a thickness of less than 1 µm, preferably a thickness of less than 0.2 µm, preferably a thickness of less than 0.05 µm. Most particularly preferable is a further embodiment, wherein no separating layer is present between heating elements and reaction volume, or wherein the thermic properties of the separating layer are selected so that their effect with regard to the heat emission of the heating means to the reaction volume is negligible.

It can be advantageous for an even, or steady, temperature to be reached as far as possible everywhere on the heating elements. This can be achieved in the case of heating resistors for example in that, in each sub-piece or sub-volume of the heating resistor, an even current density during the heating and a constant surface/volume ratio (OVV) are facilitated. This is advantageously achievable in that a constant conductor cross-section and a constant voltage drop per unit of length of the conductor are ensured in the whole heating element. In the case of a plurality of heating elements, these heat the reaction volume in a preferred embodiment of the invention in the same way. However, the invention also includes embodiments in which heating elements heat the reaction volume differently, for example for different lengths of time or with different intensities. The heating elements of the heating means can be the same or different, for example with regard to their length or geometry.

The reaction volume is preferably heated by a heating means made up of one or more heating elements, wherein particularly preferably the heating element or at least one of the heating elements, particularly preferably all the heating elements, are in contact with the reaction volume. In a preferred embodiment of the invention at least one of the heating elements abuts, on its entire surface, against the reaction volume. Particularly preferably all the heating elements abut against the reaction volume on their entire surface. It is an achievable advantage of this embodiment of the invention that the reaction volume can be efficiently heated by the respective heating element in the vicinity of the heating element. It can also be advantageously achieved through this embodiment of the invention that, in order to ensure high reaction kinetics (especially of the hybridisation kinetics of the nucleic acid molecules to primers, which, as indicated below, are preferably arranged on the heating element), the heating means has an accessible surface that is as large as possible.

It is preferable for the heating elements to have a surface/volume ratio (OVV) that is as high as possible in order to facilitate an emission of the heat that is as effective as possible to the (direct) vicinity, and at the same time to have a volume that is as low as possible, in order to ensure a low heat capacity of the heating element. Preferred embodiments according to the invention have a surface/volume ratio for the heating elements that is more than $10^3$ m$^{-1}$ (per metre), preferably more than $10^4$ m$^{-1}$ and particularly preferably more than $5*10^4$ m$^{-1}$. A surface/volume ratio that is too great, however, can lead in some cases to very filigree and thus mechanically unstable structures, so that it can be advantageous according to the invention to keep the surface/volume ratio less than $10^9$ m$^{-1}$, preferably less than $10^8$ m$^{-1}$ and in some cases even less than $10^7$ m$^{-1}$.

For a long wire draht (length much greater than diameter) the surface/volume ratio is calculated for example with 2/r, wherein r is the radius of the wire. For a thin film or a foil (thickness very much less than length and lateral expansion), the surface/volume ratio is calculated with 1/d, wherein d is the thickness of the film or the foil. According to the invention it is preferable, for the above embodiments, to take into consideration only the surface that is in contact with the reaction volume. It is also preferable to take into consideration only the volume of which surface(s) is/are in contact with the reaction volume (i.e., for example, inlet lines that do not run through the solution are not to be regarded according to the invention as relevant volumes and surfaces). The same also applies correspondingly to the subsequent consideration of volume fill factor and heat capacity.

In a preferred embodiment of the invention the ratio between the surface of the heating means that is in contact with the reaction volume and the reaction volume is greater than 0.1 m$^{-1}$, particularly preferably greater than 1 m$^{-1}$, particularly preferably greater than 5 m$^{-1}$, particularly preferably greater than 10 m$^{-1}$, particularly preferably greater than 20 m$^{-1}$, particularly preferably greater than 50 m$^{-1}$, particularly preferably greater than 100 m$^{-1}$. This embodiment of the invention advantageously enables favourable reaction kinetics to be achieved in that, in a large proportion of the reaction volume, constituent parts of the reaction volume can rapidly reach the surface of the heating element through diffusion, in order to participate in the steps of the nucleic acid amplification method taking place there. Also, in the case described further below for heating elements, which are functionalised at least in part on their surface with one of the reaction partners (for example a primer), it is possible to utilise the fact that more reaction partners are also available through a larger surface.

In order to prevent the heating element structure becoming too filigree or the movement of the nucleic acid molecules and other reactants located in the reaction volume being hindered by too many surfaces, the ratio of the surface of the heating element or the heating elements in the ratio to the size of the reaction volume is less than 10$^6$ m$^{-1}$, particularly preferably less than 10$^5$ m$^{-1}$, particularly preferably less than 10$^4$ m$^{-1}$, and most particularly preferably less than 10$^3$ m$^{-1}$.

In order to keep the heat supplied by the heating means to the reaction volume in the denaturation step as low as possible, it can be advantageous to also keep the heat capacity of the heating means low, as, in order to achieve a certain temperature increase on the surface of the heating elements: an increasingly large amount of energy is required, the greater the heat capacity of the heating means. The amount of energy supplied to the reaction volume by the heating means in the denaturation step subsequently spreads over the whole reaction volume. The heat capacity of the heating element is given by the product of the respective volume and the specific volumetric heat capacity of the respective material, from which the respective volume is made. A significant degree of freedom in the configuration of the heating means is in its dimensions.

It can therefore be advantageous to keep the volume of the heating means, in particular the material thickness, as low as possible. It is noteworthy in this respect that the heat diffusion range does not depend on the size of the heating means but instead merely on the heating duration. In a preferred embodiment of the invention the volume of all the heating elements of the heating means is less than 10%, preferably less than 5%, particularly preferably less than 3% and most particularly preferably less than 1% of the reaction volume. With this embodiment of the invention, a low heat capacity of the heating means can advantageously be achieved through a low volume fill factor.

In a preferred embodiment of the invention the heating means comprises an arrangement of a plurality of conductors with current flowing through them, which are surrounded by the reaction volume. It is can advantageously be achieved here that the heating means can be effective at many different places, or parts, of the reaction volume. This is particularly favourable in typical cases, in which at the start of a PCR there is only a very low concentration of nucleic acid molecules to be amplified and the average distance of these molecules from the nearest heating element is therefore long. It can be estimated that a nucleic acid single strand with a length of 100 base pairs requires a time $t=x^2/D_{DNA}$ in order to move itself, through diffusion, over a distance x from its starting point (wherein $D_{DNA} \approx 10^{-11}$ m$^2$/s). In a preferred embodiment of the invention the spatial distance of a given point in the reaction volume from the nearest heating element is less than 3 mm (millimetres), preferably less than 2 mm, particularly preferably less than 1 mm, particularly preferably less than 0.75 mm, particularly preferably less than 0.5 mm and particularly preferably less than 0.25 mm.

In an embodiment of the invention one or all of the heating elements is/are made from an electrically conductive metal or a metal alloy or another electrically conductive material with low specific electrical resistance for example carbon, a semiconductor material or a conductive plastic.

In one embodiment, one or all of the heating elements consist(s) only of one wire or one electrical conductor or a plurality of wires or electrical conductors. These can be straight, bent or wound in a coil. A plurality of wires or electrical conductors can have an equal or unequal distance from each other, can cross each other or not cross each other. Each wire or electrical conductor can have a round, oval, planar or any other cross-section. A heating element can also be simply a passable, i.e. a pass-though, surface area, for example a flat surface damped with metal.

A particularly preferred embodiment of the heating means is an arrangement, or array, preferably a periodic arrangement, of conductive metal wires. Particularly preferably the wires are arranged parallel to each other. The wires of the array preferably have a diameter of between 0.5 and 100 μm (micrometres), particularly preferably between 1 and 50 μm. The wires are preferably spaced apart from each other by between 50 and 1500 μm.

The wires preferably are made of gold or other metals, or they are designed as sheathed wires, wherein the core consists of a cheaper and more stable material, preferably a metal. Particularly preferable are sheathed wires with stainless steel, molybdenum or most particularly preferably with a tungsten core with a sheath of an inert material, preferably gold. Due to the high strength of the core, such wires can advantageously be designed to be very thin (and thus with a high surface/volume ratio), but still facilitate, through the sheath material, still the desired chemical properties of the preferably stainless steel sheath. Particularly preferred are sheathed wires with a tungsten core (tungsten advantageously has a much higher tensile strength than gold), preferably with a core diameter of between 5 and 40 μm and a gold sheath with a thickness of between 0.1 and 2 μm.

In another embodiment metallic foils are used as the heating element, which traverse the reaction volume and which designed as lattices, for example through stamping/punching, electroforming, laser or hydro-jet cutting, etching technology or other methods.

In another embodiment of the invention the heating element is applied to a material that is not electrically conductive or which has poor electrical conductivity. Preferred heating elements are made of a metallic film, which has been applied to a non-conductive structure galvanically, chemically, through PVD, through pressure methods or other methods. The non-conductive structure can for example be designed as a very fine injection moulded part (a preferred structure size is less than 300 μm) or through a rapid prototyping method. Fabric structures can also be considered for use as heating elements or carriers for heating elements. In particular such materials with a mesh size of between 20 μm and 3 mm, particularly preferably between 100 μm and 1.5 mm, can be used as heating elements or as carriers for heating elements. If the fabric structures themselves are conductive, they can advantageously be used in their entirety as a heating element. If they are made of non-conductive material (for example a plastic), they can be metal-plated, so that the current flows only through a thin surface layer (typically <10 μm) and so that there is a large surface. In other words, the wires or fibres of the fabric of lattice have a comparatively large surface, but only the thin, applied metallic volume is actively heated. In the sense of the invention it is only the part through which the current essentially flows that is to be regarded as the heating element. If for example a plastic structure of PMMA with a gold film is evaporated, then only the gold film to be regarded as a heating element.

Functionalisation of the Heating Means

In a preferred embodiment of the invention at least one of the heating elements of the heating means is conjugated to oligonucleotides, i.e. oligonucleotides are joined to the heating element. Particularly preferably all the heating elements of the heating means are conjugated to oligonucleotides. In this way it can advantageously be achieved that oligonucleotides that are parts of the method according to the invention are specifically heated by the heating means without the whole reaction volume having to be heated. In a particularly preferred embodiment of the invention the heating element(s) is/are conjugated to primers, most particularly preferably to forward and reverse primers of the PCR method. In a preferred embodiment of the invention forward primers, but no reverse primer, are attached to a heating element or a portion of a heating element, and/or reverse primers, but no forward primers, are attached to a heating element or a portion of a heating element. The molecules of the other primer, in each case, can be freely suspended in the reaction volume. If a separating layer is used between heat generating components of the heating means and the reaction volume, the functionalisation must be realised in such a way that oligonucleotides are accessible from the liquid volume, i.e. they are preferably attached on the surface of the separating layer.

In a further preferred embodiment, at least one of the heating elements is conjugated to forward primers and also to reverse primers. In a particularly preferred embodiment all heating elements of the heating means are conjugated to forward primers and also to reverse primers. With this embodiment of the invention, it can advantageously be achieved that the PCR product of a forward primer, for hybridisation with the reverse primer of the same heating element, only needs to travel a short distance, with the result that a hybridisation can take place more quickly and therefore the PCR method can be carried out more quickly.

In a preferred embodiment of the invention a heating element is provided at its surface with a material that allows the bonding of nucleic acids. For example a gold-plated surface can be used in order to bind a primer via one or more thiol bond(s) on a heating element. Also, for example a streptavidin biotin bond can be used to bind a primer to the heating elements if, for example, preferably beforehand, one of the two partners (streptavidin or biotin) has been bonded to the heating elements and the primer (at the 5'-end) is modified with the other of the two partners and subsequently thereby bonded to the heating element. Other modifications such as, for example, amino or carboxy groups, can also be used to bind primers to the heating elements; for this purpose, the surface of the heating element can for example, preferably beforehand, be modified with epoxy. A bond is preferably realised in such a way that the 5'-end of the primer is bonded to the heating elements, so that the 3'-end is free and can therefore be elongated during the PCR by the polymerase.

In the embodiment in which both forward primers and also reverse primers are immobilised on a heating element, the distance between the primer molecules of different types can purposefully be selected to that on average they are at a distance from each other of, for example, less than 1 nm (nanometre), less than 3 nm, less than 5 nm, less than 15 nm or less than 50 nm. With this embodiment, it can advantageously be utilised that, as soon as a forward primer has been elongated on the surface of the heating element, this newly written nucleic acid strand hybridises, after denaturation, to a corresponding adjacent reverse primer molecule on the surface or to a reverse primer molecule in the vicinity. As this process takes place on the surface of the heating elements, the local concentrations are extremely high. The new nucleic acid strand does not therefore have to travel many micrometres through diffusion in order to find a reverse primer molecule, because in the direct vicinity —only a few nanometres away—there are many reaction partners (the same applies, vice versa, to elongated reverse primer molecules, which find immobilised forward primer molecules in the vicinity).

In one embodiment, besides the primer molecule(s), there are also fill oligonucleotides or fill molecules on the heating elements, i.e. oligonucleotides or molecules that do not actively participate as primers or fluorescence probe or target nucleic acid in the PCR, but instead merely serve for surface saturation or passivation, in order to prevent a nonspecific (thus not through targeted hybridisation with primers) binding of am amplicon or a target nucleic acid to the surface of the heating element. Fill oligonucleotides preferably have a length of between 5 and 50 nucleotides, particularly preferably between 10 and 40 nucleotides and most particularly preferably between 20 and 30 nucleotides. In particular they can consist only of a nucleotide type, for example A30 sequences with 30 adenine bases. Fill molecules can for example be biotin or polyethylene glycol, for example additionally provided with a functional group such as for example thiol, in order to immobilise the fill molecules on the heating element surface. However, fill molecules can also be for example bovine serum albumen.

In a further preferred embodiment of the method the oligonucleotides on the heating elements have a spacer sequence as a sub-sequence. The spacer sequence is thereby on the side, facing towards the heating, of the respective oligonucleotide. The spacer sequence thus serves as a spacer for the rest of the oligonucleotide. In a preferred embodiment an oligonucleotide contains both a sub-sequence, which has the function of a primer and is described as a primer sequence, and also a sub-sequence that is a spacer sequence. Due to the fact that the primer sequences are spaced further apart from the heating elements by the spacer sequences, the nucleic acids to be amplified and the DNA polymerases advantageously have better access to the primer sequences.

In a preferred embodiment of the method according to the invention, there is one or more non-basic (abasic) modification(s) between spacer sequence and primer sequence, these abasic modifications preventing the overwriting of the spacer sequence by the polymerase.

The content of the patent application DE102013215168 is hereby incorporated by reference. Such modifications can be for example: 1',2'-dideoxyribose (dSpacer), triethylene glycol spacer (spacer 9) or hexaethylene glycol spacer (spacer 18), which prevent the further polymerase activity in 3'-direction. In this way it can be achieved that the spacer sequence does not serve as a template for the nucleic acid strand synthesised by the polymerase and the resulting PCR product does not become unnecessarily long. An elongated PCR product, which also contains the complementary sequence to the spacer sequence, would have a significantly increased melt temperature with the oligonucleotides on the nanoparticles and would hybridise unnecessarily non-specifically in subsequent hybridisation steps and thus make the whole PCR more nonspecific.

Duration of the Heating

The heat supply through the heating means preferably varies during the PCR. Particularly preferably the heat supply through the heating means varies during at least one passage of the amplification cycle of the PCR, particularly preferably during at least three, particularly preferably in at least 10, particularly preferably in at least 20, of the passages of the amplification cycle of the PCR, particularly preferably periodically.

The duration of the heating by the heating means in the denaturation step (hereinafter the heating by the heating means in the denaturation step is also referred to as "heat pulse") in a preferred embodiment of the invention is, in at least one, preferably in at least three, particularly preferably in at least 10, particularly preferably at least 20 of the passages of the amplification cycle of the PCR, is in the interval between 100 ns (nanoseconds) and 30 ms, particularly preferably between 0.5 μs (microseconds) and 10 ms, particularly preferably in the interval between 1 μs and 5 ms, particularly preferably between 1 μs and 3 ms, particularly preferably between 1 μs and 1 ms, particularly preferably between 1 μs and 800 μs, and most particularly preferably in the interval between 1 μs and 500 μs. An achievable advantage of this embodiment of the invention is a localisation of the heat and thus the resulting temperature distribution. In other words, due to the short heating duration, limited heat is transported by the heating element through heat diffusion into the solution. At the same time it can be achieved with this embodiment of the invention that the heating duration is not too short to allow a sufficient melting or extrication of the nucleic acid double strands during the time of the local heating, and/or to enable, during the time of the local heating, both single strands to be able to move sufficiently far away from each other through Brownian motion (and/or other forces) so that they do not re-hybridise to each other.

In a preferred embodiment of the invention the duration of the denaturation step accounts for only a small fraction of the total duration of the PCR. Preferably the denaturation step accounts, during at least one passage of the amplification cycle, particularly preferably during at least three, particularly preferably during at least 10, particularly preferably during at least 20 of the passages of the amplification cycle of the PCR, less than 10%, furthermore preferably less than 5%, particularly preferably less than 3%, particularly preferably less than 1%, particularly preferably less than 0.5%, particularly preferably less than 0.05%, and particularly preferably less than 0.01% of the time taken by the entire passage of the amplification cycle of the PCR. Through this embodiment of the invention it can advantageously be achieved that hybridisations can take place during virtually the entire duration of the PCR. As the polymerase in the local PCR can work for virtually the entire duration, the process time can be shortened. It is also achievable that, due to the heating being realised only locally realised and in addition very short heating, the participating polymerase enzymes and also other reaction partners are protected and they lose their processivity less quickly.

In a preferred embodiment of the invention, during at least one passage of the amplification cycle, particularly preferably during at least three, particularly preferably during at least 10, particularly preferably during at least 20 of the passages of the amplification cycle of the PCR, the duration of the denaturation step $t_{heat}$ is shorter than $t_{heat} \leq (s1 \cdot |x|)^2/D$, wherein s1 is a scaling factor, $|x|$ is the critical distance and D is the temperature conductivity. The scaling factor s1 is preferably s1=100, particularly preferably s1=10, particularly preferably s1=1, particularly preferably s1=0.1, particularly preferably s1=0.01. The critical distance $|x|$ is the distance from the nearest indirectly adjacent part of the heating means, for example from the nearest heating element of the heating means. If the heating element(s) is/are constructed from a 2D structure (for example a lattice, fabric, honeycombs, etc.), the mesh size or the size of the holes/recesses is the relevant value $|x|$. If the heating element(s) consist(s) of a 3D structure, the pore size is the relevant value $|x|$.

It can be achieved with this embodiment of the invention that the heating duration is so short that the heat diffusion range is much smaller than the average distance $|x|$, thermal fields of adjacent heating elements or generally adjacent, non-abutting parts of the heating means do not therefore overlap. In particular, scaling factors greater than 1 can be advantageous for very long amplicons, wherein the disentangling of the two nucleic acid strands takes longer (the time taken until a nucleic acid double strand can disentangle through Brownian motion) increases to the fourth power of the length. Scaling factors below 1 can be advantageous for the best possible heating and cooling dynamics.

Electricity Storages

A preferred device according to the invention is configured so that its electrical power consumption does not at any time during the PCR exceed 50 W, particularly preferably 20 W, particularly preferably 10 W, particularly preferably 3 W, particularly preferably 2.5 W, particularly preferably 1.5 W, particularly preferably 0.5 W. This limitation does not apply to possibly higher power consumption during the switch-on process of the device, as may be caused for technical reasons by switch-on currents. Such increased power consumptions are not regarded as power consumptions during the PCR and are not therefore taken into consideration here. With this embodiment of the invention it can advantageously be achieved that the device can be operated on common portable power sources, for example on a motor vehicle battery, on the cigarette lighter of a motor vehicle or on a port of a PC, a tablet computer or a mobile phone, for example on an USB or an Apple lightning connection.

The device preferably comprises an electricity storage. It is preferably designed so that the electrical energy retained in the electricity storage, in relation to the capacity of the reaction vessel, is greater than 0.1 J/mL, particularly preferably greater than 1 J/mL, particularly preferably greater than 2 J/mL, particularly preferably greater than 3 J/mL. The electricity for the electricity requirements of the heating means, which also varies due to varying heat supply, can be intermediately stored with the electricity storage.

A device according to the invention comprising an electricity storage is preferably designed so that the electrical energy retained in the electricity storage energy, in relation to the capacity of the reaction vessel, is less greater than 100 J/mL, particularly preferably less than 50 J/mL, particularly preferably less than 30 J/mL. This embodiment of the invention can utilise the fact that, due to particularly efficient heating through the heating means, the electricity storage can have a small configuration. In this way the device according to the invention can advantageously be designed to be particularly compact, cost-effective and portable.

A preferred electricity storage comprises one or more capacitor(s), coil(s), or battery/batteries or a combination of the aforementioned. In a preferred embodiment of the invention the storage capacity of the energy storage is configured so that it can hold, in an available form, at least 20%, particularly preferably at least 40%, particularly preferably at least 50%, particularly preferably at least 60%, particularly preferably at least 80%, particularly preferably at least 100%, particularly preferably at least 150%, particularly preferably at least 200%, particularly preferably at least 300% of the electrical energy required for the denaturation step of a passage of the amplification cycle of the PCR. With this embodiment of the invention, the situation of a power source having to be made available that can provide the electrical power required for the denaturation step over the whole duration of the denaturation step can be avoided. Instead, advantageously in the time between the denaturation steps, which is generally considerably longer than the duration of the denaturation step, the energy storage can be charged up. In this way it can be achieved that the device according to the invention can be equipped with a power source that is weaker in relation to its electrical output, for example with a weaker network device. If the electricity storage provides less than 100% of the energy required for the denaturation step of a passage of the amplification cycle of the PCR, it can advantageously be kept very small, but the remaining energy must then be provided by an additional, correspondingly dimensioned power source, for example a power network connection, during the denaturation step. Values of 100% and more are advantageous, as the power source supplying the capacitor(s) can then be kept correspondingly small and in addition the voltage does not collapse due to the load of the heating. In particular it can advantageously be achieved that a power source of the device according to the invention merely needs to have such dimensions that it is able to provide the amount of energy required for the denaturation step over the duration of an amplification cycle of the PCR, but not already during the significantly shorter denaturation time.

In a preferred embodiment of the invention, in at least one, preferably in at least three, particularly preferably in at least 10, particularly preferably in at least 20 of the passages of the amplification cycle of the PCR, the ratio between the electrical power consumption of the device and the capacity of the reaction vessel does not at any time during the PCR exceed 1 W/mL, preferably 0.5 W/mL, particularly preferably 0.25 W/mL, particularly preferably 0.1 W/mL. This limitation does not apply to possibly higher power consumption during the switch-on process of the device, as may be caused for technical reasons by switch-on currents. Such increased power consumptions are not regarded as power consumptions during the PCR and are not therefore taken into consideration here In a preferred embodiment of the invention the electricity storage is configured so that it can hold, in an available form, the energy for the denaturation steps of at least 5, particularly preferably at least 10, particularly preferably at least 20, particularly preferably at least 40, particularly preferably at least 100 passages of the amplification cycle of a PCR. In this way a device, in particular a portable device, can advantageously be created that can carry out one or even several polymerase chain reactions independently of another power source.

Preferred capacitors are high-capacity capacitators, preferably electrolyte capacitors or super-caps, particularly preferably having a low ESR value. Such capacitors can be obtained cost-effectively on the market and are easy to dimension. For example, using the equation $Q=½C^U$ or $C=2·Q/U^2$, it can be calculated that a capacitor with a capacitance of 2222 µF (microfarad) would be sufficient for the provision of 1 J (Joule) of electrical energy-which would suffice, with virtually loss-free conversion of the electrical energy into heat, according to an embodiment for the denaturation step of a reaction volume of 1 mL—with a voltage U of 30 V. However, the capacitor would then be completely discharged at the end of the heat pulse, so that in practice the use of a capacitor with at least 1.5 times higher capacitance is recommended if the power source cannot supply a considerable part of the power.

In a preferred energy storage according to the invention the capacitance of the capacitor, or, in the case of a plurality of capacitors, the sum of the capacitances of this plurality of capacitors, is greater than 100 µF, particularly preferably greater than 200 µF, particularly preferably greater than 500 µF, particularly preferably greater than 1 mF (millifarad), particularly preferably greater than 1.5 mF. In a preferred energy storage according to the invention the RATIO between the capacitance of the capacitor, or, in the case of a plurality of capacitors, the sum of the capacitances of this plurality of capacitors, and the size of the reaction volume is greater than 0.01 mF/mL (millifarad per millilitre), particularly preferably greater than 0.1 mF/mL, particularly preferably greater than 1 mF/µL, particularly preferably greater than 5 mF/mL, particularly preferably greater than 10 mF/mL. With this embodiment of the invention, sufficient energy can advantageously be intermediately stored to achieve sufficient heating of the heating element in the denaturation step.

Particularly preferred batteries are high-current batteries or accumulators, in particular lithium-polymer accumulators, lithium-ions or lithium-iron phosphate accumulators. In one embodiment of the invention the battery/batteries is/are used with one or more capacitors. In another embodiment the battery/batteries, is/are particularly preferably lithium-iron phosphate accumulators, which are characterised by an advantageously low internal resistance, without additional use of a capacitor. It can be favourable according to the invention if the inlet lines running between capacitor(s) and/or batteries and as far as the heating element are as short as possible, in order to reduce interference-causing inductances and ohmic resistances of the inlet lines.

Reaction Vessel

A preferred device for the amplification of nucleic acids has a reaction vessel for receiving the reaction volume. Suitable reaction vessels of the method according to the invention can be conventional PCR reaction vessels such as PCR tubes or composites of PCR tubes (such as, e.g., so-called 8 stripes) or multiwell plates, but also, for example flat plates or other shapes/forms that can be filled. The heating means can be brought into the reaction vessels, for example wires that pass through the walls of multiwell plates or PCR tubes, already during the production process (for example injection moulding), or be added after the production process (as for example in the case of wires in the form of coils, which can be suspended in the individual wells of a multiwell plate).

Control Device

A preferred device according to the invention comprises a control device, which applies electrical current to the heating means in order to heat the reaction volume. The control device is preferably configured so that, in at least one, preferably in at least three, particularly preferably in at least 10, particularly preferably in at least 20 of the passages of the amplification cycle of the PCR, the ratio between the electrical energy used in the denaturation step to heat the reaction volume and the capacity of the reaction vessel is less than 40 J/mL (Joule per millilitre), particularly preferably less than 20 J/mL, particularly preferably less than 10 J/mL, particularly preferably less than 3 J/mL.

In a preferred device according to the invention the control device is configured so that at least one heating element of the heating means has in at least one direction an expansion of more than 1.5 μm. Particularly preferably each heating element of the heating means has, in at least one, particularly preferably in two, direction(s), an expansion of more than 1.5 μm. The expansion can for example be a length or a diameter of an elongate heating element. A preferred elongated heating element has a diameter of at least 1 μm, particularly preferably at least 2 μm, particularly preferably at least 5 μm. A preferred elongate heating element has a length of at least 0.1 mm, particularly preferably at least 1 mm, particularly preferably at least 2 mm. In the case of a network-form or honeycomb-formed heating element the expansion can also be, for example, also the thickness (meaning the expansion of the webs perpendicularly to the surface of the network-form or the honeycomb) or the diameter of the webs. Preferred webs have a thickness or a diameter of at least 1 μm, particularly preferably at least 5 μm, particularly preferably at least 10 μm.

The preferred control device is designed so that it allows, or increases, a current flow through the heating means at the start of the denaturation step—or at the start of each time interval of the denaturation step if the denaturation step is composed of a plurality of time intervals separated from each other, and again suppresses, or reduces, said current flow after the end of the denaturation step—or after the end of each time interval of the denaturation step—in order to bring about a current pulse. In the heating element the current pulse can be converted into a heat pulse. The preferred control device comprises a power source, which for its part can comprise for example a power network component, one or more battery (batteries) or accumulators or fuel cells. The preferred control device comprises one or more capacitors. The preferred control device comprises a switch, which, preferably with a selectable time duration, can switch on and off the current flow from the power source through the heating means. Suitable switches include MOSFETs, SSRs, very rapid relays and transistors. The control device can have one or more pulse or frequency generators, DACs or microcontrollers for time control.

Observation of the PCR and Detection of PCR Products

Preferably in the method according to the invention amplicons are detected or the original presence of the target nucleic acid in the sample is detected. This can be realised for example through gel electrophoresis after the PCR, hybridisation of the amplicon to immobilised oligonucleotides, which are complementary to the amplicon or parts thereof, through a detection by means of, for example, fluorescent dyes or through a detection via electronic methods. In a further preferred embodiment, a real-time detection takes place already during the PCR in the reaction volume in order to observe the progress of the polymerase chain reaction with the aid of an optical method.

For this optical methods are particularly preferred, in particular fluorescent methods, for example in the TaqMan format. The relevant disclosure of U.S. Pat. No. 5,210,015 A and the publication by Holland et al. Proc Natl Acad Sci USA, 88 (16), 1991, pages 7276 to 7280, are hereby incorporated by reference. In this method a specific fluorescent signal is produced during the PCR, which allows the real-time observation of the amplification reaction and even a quantification of the number of target nucleic acids originally used. Other real-time detection methods are also possible, for example the use of intercalating dyes such as SybrGreen and the use of molecular beacon probes. However, the invention also includes embodiments, in which the amplification of the nucleic acids is purely preparative in the sense that the amplicon is used further for example in a subsequent process.

A preferred device according to the invention comprises a light source, for example a semiconductor light source, for example a light emitting diode or a laser diode. Dyes can advantageously be excited in the reaction volume with the light source, preferably in order to observe the progress of the polymer chain reaction with the aid of an optical method.

A preferred device according to the invention comprises a light sensor, for example a semiconductor light sensor, for example a photodiode. Dyes can advantageously be detected in the reaction volume with the light sensor, preferably in order to observe the progress of the polymer chain reaction with the aid of an optical method. The light sensor can be equipped with one or more filters.

Where reference is made to "light" in connection with detection or observation methods relating to this invention, this includes all possible types and wavelengths of light that are suited for optical detection methods, in particular also those suited for excitation or detection of a fluorescent dye. The light is preferably visible light, but it can also be ultraviolet or infrared light. The light can be laser light.

BRIEF DESCRIPTION OF THE DRAWINGS

FIGS. 3B, 3C, 3D show possible embodiments of reaction vessels that contain heating elements.

DETAILED DESCRIPTION OF THE INVENTION BY REFERENCE TO A PLURALITY OF EMBODIMENTS

Figure 1A:
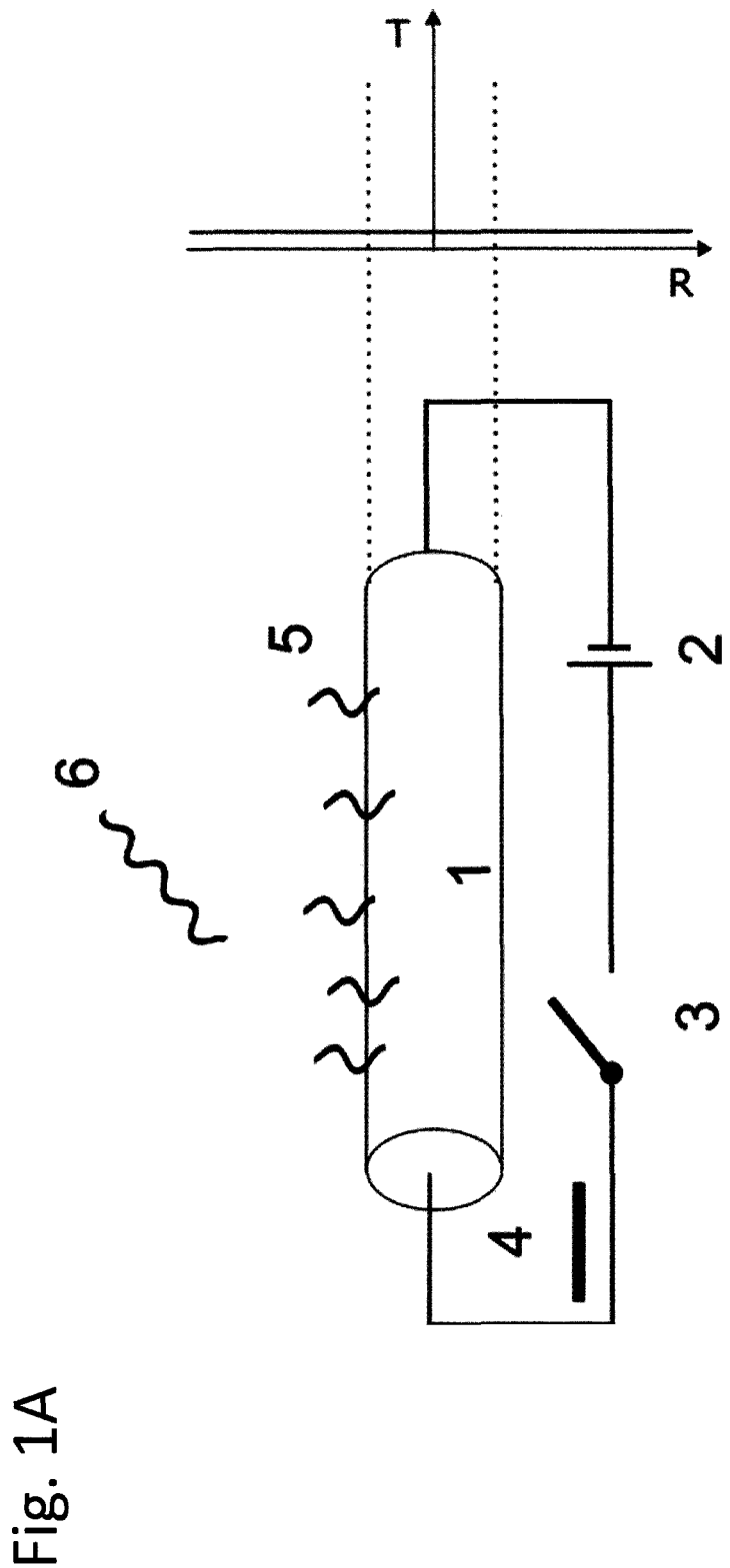
FIG. 1A shows schematically a heating element functionalised to primers, through which there is no current flow, as the switch is open. There is a free DNA sequence in the vicinity of the heating element'.

Course of the Method According to the Invention

By way of example, the first passage of the amplification cycle of the PCR can be carried out as follows in a method according to the invention: After the addition of nucleic acid molecules (hereinafter described as "target nucleic acids") to the reaction volume (and possibly the denaturation thereof by global heating) and the hybridisation thereof to forward primers bonded to one or more heating element, a polymerase elongates the forward primers and thereby produces complementary strands for the target nucleic acid. The denaturation, i.e. the separation of the molecules of the target nucleic acid from the elongated forward primers, is not realised by global heating of the whole reaction volume, but instead through a heat pulse, which is brought about by a current pulse through the heating element(s) of the heating means.

The subsequent second passage of the amplification cycle of the PCR can be realised in a similar way. The molecules of the original target nucleic acid hybridise again to forward primers bonded to one or more heating element(s) and the polymerase elongates the forward primers and hereby produces complementary strands for the target nucleic acid (or at least for a proportion of the target nucleic acid), In parallel, reverse primers (which are either freely suspended or also heating element-bonded) can bind to the elongated parts of the elongated heating element-bonded forward primers produced in the first passage of the amplification cycle of the PCR (the forward primers now constitute complementary strands to at least a proportion of the target nucleic acid) and the reverse primers are subsequently correspondingly elongated by the polymerase. In this way, for the first time genuine copies of at least a part of the original target nucleic acid are produced. The denaturation, i.e. the separation of the double strands produced through elongation by the polymerase (the double strands are in any case again bonded to the heating means) is realised once again through a heat pulse caused by the current pulse through the heating means. With effect from the third passage of the amplification cycle of the PCR, both the original target nucleic acid and also the nucleic acid strands produced by elongation of the primer sequences through the polymerase (depending on the embodiment: freely suspended in the reaction volume or heating element-bonded) as a template for the further amplification. They are amplified by hybridisation to corresponding primers (according to the embodiment: freely in solution of bonded to a heating element), there is subsequent elongation by through the polymerase and then denaturation by means of a local heat pulse, which is brought about by a current impulse through the heating means. The last described passage of the amplification cycle of the PCR is repeated several times in order to produce further copies at least of parts of the target nucleic acid in each further passage of the cycle. The passages are repeated until as often as necessary until a sufficiently high number of copies at least of parts of the target nucleic acid are present in order to be able to carry out a detection of the amplification carried out or the original presence of the target nucleic acid in the sample. Using one of the methods described above, for example fluorescence method, the thus generated amplicons can be detected.

In a further exemplary embodiment of the invention a plurality of different target nucleic acids are amplified in parallel (also described as "multiplex-PCR"). For this, a plurality of primer pairs that are different from each other (in each case: forward and reverse primers) are necessary for each amplicon (wherein a primer can also serve as a primer for two amplicons, for example of different lengths, therefore being part of two primer pairs). A heating element can carry a plurality of primer pairs or in each case (at least) one primer made up of a plurality of primer pairs. However, a plurality of primers or primer pairs can also be distributed in such a way that different sub-portions of the heating element each carry only one primer pair or each carry only one partner of a primer pair. In an exemplary embodiment one (possible only one per primer pair or even each) primer sort or primer sequence can be present in both a heating element-bonded form and also freely suspended form in the reaction volume.

A detection can be realised for example by using different dyes in such a way that different colour signals are produced (with different wavelengths) can be assigned to the formation of different amplicons. Alternatively, however, different amplicons can also produce the same colour signals, which cannot be differentiated. Different amplicons can also be differentiated, for example using gel electrophoresis or other methods.

Setting, or Establishing, a Global Reaction Temperature

The (global) elongation and hybridisation temperature is kept constant in a preferred exemplary embodiment during the whole course of the PCR, for example by means of a conventional external heater, for example a temperature-regulating block, or through a constant (or regulated) excitation of the heating element by means of a constant (or regulated) offset current through the heating element.

The regulation of the (global) elongation and hybridisation temperature or the heating temperature can be realised on a temperature sensor in the reaction volume, in one of a plurality of reaction volumes, individually for each individual reaction volume through a respective sensor in the respective reaction volume, by a sensor outside of the reaction volumes or through a sensor in the heater or a recording device for the reaction volume. In one embodiment the (global) elongation and hybridisation temperature for all reaction volumes is the same, in a further embodiment the (global) elongation and hybridisation temperature can differ for the different reaction volumes.

In a further embodiment the (global) elongation and hybridisation temperature can be varied or changed during the duration of the PCR or before or after the PCR. In one embodiment the heater can also consist of a plurality of parts, for example from a bottom part and a top part, wherein the top part has a somewhat higher temperature than the bottom part in order to avoid condensation on the walls of the reaction volumes. The temperature difference between the top and bottom part of the heater is preferably between 1° C. and 30° C., particularly preferably between 2° C. and 20° C. and most particularly preferably between 3° C. and 15° C.

In one embodiment the global heating of the reaction liquid in the reaction vessel through electrical heating of the heating means can account for a part of the heat input or all of the heat that is required to reach the desired elongation and hybridisation temperature. This can for example be achieved by the duty cycle and/or the continuous electrical current (or voltage at) the heating element(s) of the heating means being selected so that the global heating of the reaction liquid in the reaction vessel in thermal equilibrium or at the end of the PCR or at the start of the PCR or during a large part of the duration of the PCR leads to the desired elongation and hybridisation temperature in the reaction liquid. The external heating (i.e. the element for the heat input that does not come through the heating element) can thereby have smaller dimensions or be completely omitted.

Preferred temperatures according to the invention for the combined hybridisation and elongation temperature are preferably between 30° C. and 85° C., particularly preferably between 40° C. and 80° C., particularly preferably between 50° C. and 75° C. and most particularly preferably between 55° C. and 72° C.

In one embodiment, a global heating step (with a global temperature greater than the later hybridisation and elongation temperature) can take place before the first actual passage of the PCR cycle, wherein said global heating step can serve for initial denaturation of the double-stranded present target nucleic acid (DNA or RNA or other nucleic acid) and/or for thermal activation of other reaction partners of the PCR such as for example (hot-start) polymerases and/or for deactivation of constituent parts of the reaction volume, which are to be active before the PCR but not during the PCR (such as for example the enzyme Uracil-DNA-glycosylase).

In one embodiment, a further global heating step with a lower global temperature than in the abovementioned global heating step can take place before this global heating step, wherein the further global heating step can be utilised for example, an enzyme being given off, a reaction taking place before the PCR (such as for example the overwriting of RNA into DNA by a transcriptase enzyme).

Spatial Heat Spreading During and after the Denaturation Step

As soon as the current flow through the heating element in the denaturation step has begun, the heating element begins to heat up. As most current-conducting materials (in particular metals) also convey heat very well, the heating element heats approximately homogeneously over the duration of the heat pulse. At the surface of the heating element, which is surrounded in a preferred exemplary embodiment by the aqueous reaction volume, the heat is transferred to the reaction volume, where it spreads. The spreading of a thermal field is realised in the reaction volume through heat diffusion, for which a root-form rule applies.

$$d \approx \sqrt{D \cdot t} \qquad \text{Equation 1}$$

wherein d describes the path distance covered by a heat front after a time t along a spatial direction in a reaction volume with temperature conductivity D and is to be referred to below as "heat diffusion range". This means, that for a heating duration of for example 100 μs, the heat generated in the heating element can diffuse far into the reaction volume with a typical temperature diffusivity (also known as "temperature conductivity") of D≈1.6·10⁻⁷ m²/s in terms of value $$d \approx \sqrt{\frac{1.6 \cdot 10^{-7} \text{m}^2}{\text{s}} \cdot 10^{-4} \text{s}} \approx 4 \text{ μm}$$

In other words, the heat generated in the heating element for example by ohmic losses has spread after 100 μs into the reaction volume surrounding the heating element, namely with a magnitude in the range of 4 μm.

Through the spatial spread of the heat corresponding to the above equation the amount of heat brought is distributes over an increasingly large volume so that, perpendicular to the surface of the heating element, which is hotter by a temperature $\Delta T$ than the global average temperature, a temperature gradient of the value $\Delta T/d$ results, which facilitates the heat transport. A more precise estimation of the spatial heat expansion during and after the heat pulse for the respective geometry of the heating element can be achieved by finite element methods such as, for example, with commercial solutions like for example Comsol, which facilitate a numerical solution of the heat diffusion equation. The reaction volume within a layer with the thickness of a heat diffusion range is preferably heated around the heating means by at least more than 10° C.

In a preferred embodiment of the invention the heat diffusion range in at least one, preferably in at least three, particularly preferably in at least 10, particularly preferably in at least 20 of the passages of the amplification cycle of the PCR, at the end of the denaturation step is preferably between 0.05 μm and 200 μm, particularly preferably between 0.2 μm and 100 μm, particularly preferably between 0.5 μm and 50 μm and most particularly preferably between 1 μm and 25 μm. It is an achievable advantage of this embodiment of the invention that on the one hand a sufficient spatial expansion of the heated area perpendicular to the surface of the heating element can be achieved and that the PCR amplicons formed on the heating element, which typically have a length of between 0.02 and 3 μm (correspondingly roughly between 60 and 10000 base pairs), can be heated as homogeneously as possible and thus denatured, and that the heat diffusion range is not so large that the volume ratio of the heating-up zone to the unheated passive volume becomes too low.

In the sense of the present invention the "heating-up zone" is the part of the reaction volume, in which the heat can diffuse during the denaturation step. The expansion of the expansion of the heating-up zone perpendicular to the surface of the heating element can be estimated approximately through the heat diffusion range defined above. The volume of the reaction liquid that is not in the heating-up zone is referred to as "unheated passive volume". This means for example in the case of a cylindrical heating element (for example a heating wire) that the heating-up zone can be estimated as the volume located at the distance of a heat diffusion range d from the cylinder surface (i.e. the cylinder shell with thickness d). If the heating element is for example an elongate cylinder with radius r and length l (for example a wire), the volume of the heating-up zone can be roughly estimated as $$V_{AHZ} \approx \pi \cdot l \cdot ((r+d)^2 - r^2).$$ Equation 2

In a preferred embodiment of the invention the volume ratio of the heating-up zone to the unheated passive volume in at least one, preferably in at least three, particularly preferably in at least 10, particularly preferably in at least 20 of the passages of the amplification cycle, at the end of the denaturation step is less than 10%, preferably less than 5%, particularly preferably less than 2%, particularly preferably less than 1%, particularly preferably than 0.5%, particularly preferably less than 0.25% and most particularly preferably less than 0.1%. With this embodiment of the invention a high localisation of the heat can be achieved, which means that the amount of heat brought in the denaturation step can spread after the denaturation step to the unheated passive volume. As the unheated passive volume is many times greater than the heating-up zone, the distribution of the amount of heat over the whole reaction volume (=heating-up zone+unheated passive volume) can lead to a preferably negligible global temperature increase of the whole reaction volume, so that a very rapid cooling of the heating-up zone is possible and in addition the cooling process is (extensively) independent from a discharge of the heat to outside of the sample Estimation of the Local Temperature Increase in the Denaturation Step For typical denaturation temperatures of the double-stranded nucleic acid of between 85° C. and 98° C., in one embodiment a local temperature lift with respect to the combined hybridisation and elongation temperature of roughly between 20° C. and 40° C. must be reached on the surface of the heating elements and over the length of the double-stranded nucleic acid to be denatured.

In a preferred embodiment of the invention the temperature of the area of the heating means that is in contact with the reaction volume is, in at least one, preferably in at least three, particularly preferably in at least 10, particularly preferably in at least 20 of the passages of the amplification cycle of the PCR, during the denaturation step, is between 70° C. and 250° C., particularly preferably between 75° C. and 150° C., particularly preferably between 80° C. and 120° C., most particularly preferably between 80° C. and 100° C.

In a preferred embodiment of the invention the average temperature of the area of the heating means that is in contact with the reaction volume is over 100° C. With this embodiment of the invention, a particularly rapid separation of the double strand is advantageously possible. This embodiment of the invention utilises the fact that a short-term overheating of the reaction volume is also possible on the surface of the heating means without vapour bubbles forming (inter alia, on account of the high Laplace pressure due to the curvature of the surface of the heating element—see specialist literature for Young-Laplace equation.

In the case of complex geometries of the heating means and/or in order to ensure a high precision, the use of finite element methods (for example Comsol) is advisable, in order to determine the temperature of the heating element as a function of the electrical operating parameters. In such simulations, in the simplest case a constant volumetric heating density can be assumed or a current flow through the heating means can be simulated. In many cases, however, the temperature increase brought about by the heating means can be estimated by a simple calculation, which is set out by way of example below.

Firstly, the amount of heat that is released in a conductor with a current flowing through it is determined. The electrical power P, which is available during the electrical heat pulse for heating the heating element, is calculated from the resistance of the heating element R and the voltage U supplied at the heating element as $P=U^2/R$. The amount of heat Q released in the heating element is then the electrical power P times the heating duration $t_{heat}$.

$$Q = U^2 \cdot t_{heat}/R$$ Equation 3 wherein, here, a temporally constant voltage and constant resistance were assumed over the time duration of the heat pulse. If this is not the case, then the following applies:

$$Q = \int_0^{t_{heat}} U(t)^2/R(t) \cdot dt$$

If the heating means is made up in one embodiment (in portions) of homogeneous conductors with constant cross-section area, then the resistance of a homogeneous conductor R can be calculated from its cross-section area A and its length l as well as the specific conductivity G of this conductor element as $$R = \frac{1}{A \cdot \sigma}$$ Equation 4

Typical values for the specific conductivity are shown in tables in the specialist literature and are as follows for typical materials such as gold:

$$\sigma_{Au} = 4.6 \cdot 10^7 \frac{A}{V \cdot m},$$

for tungsten:

$$\sigma_W = 1.9 \cdot 10^7 \frac{A}{V \cdot m}$$

and for V2A (stainless steel):

$$\sigma_{V2A} = 1.4 \cdot 10^6 \frac{A}{V \cdot m}$$

If it is assumed that the duration of the heat pulse is so short that the energy in initially only heats the heating element(s) and the heating-up zone, the local temperature increase of the heating means, which is indeed to be heated to the denaturation temperature, can be estimated as follows:

$$\Delta T_{Local} \approx \frac{Q}{c_{MH} \cdot m_{MH} + c_{AHZ} \cdot m_{AHZ}}$$ Equation 5

Here, $C_{MH}$ describes the specific heat capacity (per unit of mass xx) of the heating element and $m_{MH}$ describes the mass thereof and also $c_{AHZ}$ the (mass-related) specific heat capacity of the heating-up zone (which is $c_{AHZ}$=4.2 J/(° C.·g) for the aqueous PCR solution) and $m_{AZ}$ is the mass of the heating-up zone. The above approximation is all the more precise, the smaller the heat capacity of the heating-up zone in comparison with the heat capacity of the heating element. This is due to the fact that the above equation does not take into consideration that the temperature rapidly falls in the heating-up zone (i.e. a solid temperature gradient forms around the heating element).

If the heating duration is selected to be so short that the size of the heating-up zone remains very small (significantly smaller than the heating element itself) and therefore its heat capacity is negligible with respect to the heat capacity of the heating element, the above equation can be simplified to:

$$\Delta T_{Local} \approx \frac{Q}{c_{MH} \cdot m_{MH}} \qquad \text{Equation 6}$$

While Equation 6 can only be applied in special cases and for very short heating durations, Equation 5 can be used as an approximation for determining the local temperature on the surface of the heating element(s), wherein it must be checked in each case from the geometry and the actual current flow how, above all, the mass of the heating-up zone can be calculated. In many cases, the mass of the heating-up zone can be estimated from its volume by taking into consideration the geometry of the heating element and also the heat diffusion range (see above).

The case that is particularly relevant according to the invention will be considered below, wherein the heating means is formed at least in portions (approximately) cylindrically and at least in portions is homogeneous and has a constant cross-section. The following calculation is to be regarded as an example for a cylindrical geometry of the heating means and can very easily also be transferred to other geometries. The mass of the heating element in Equation 5 can then be calculated from its volume and density:

$$m_{MH} = \rho_{MH} \cdot A \cdot l,$$

wherein A is the cross-sectional surface area and l is the length of the heating element (or the portion thereof considered). The amount of heat Q can then be calculated with Equation 3 and Equation 4.

With Equation 2, which describes approximately the volume of the heating-up zone, which surrounds an (approximately) cylindrical conductor portion with radius r and length l, the mass of the heating-up zone can be estimated in Equation 5 as:

$$m_{AZ} = V_{AHZ} \rho_{AHZ} = \pi \cdot l \cdot ((r+d)^2 - r^2) \cdot \rho_{AHZ},$$

wherein the density of the heating-up zone in the reaction volume is equal to the density of water ($\rho_{AHZ} \approx \rho_{H_2O} \approx 1$ g·cm$^{-3}$). Therefore, for a heating element that is (approximately) cylindrically formed and at least in portions is homogeneous and has a constant cross-section, the following estimation can be given using Equation 2, Equation 3, Equation 4, Equation 5:

$$\Delta T_{Local} \approx \frac{\frac{U^2 \cdot t_{heat}}{l}}{c_{MH} \cdot \rho_{MH} \cdot A \cdot l + c_{AHZ} \cdot \pi \cdot l \cdot ((r+d)^2 - r^2) \cdot \rho_{AHZ}}$$

For a cylindrical conductor portion, the cross-sectional area can be calculated form the radius $A = \pi r^2$, so that, together with Equation 1, the following simplification is given:

$$\Delta T_{Local} \approx \frac{U^2 \cdot \sigma}{l^2} \cdot t_{heat} \cdot \frac{l}{c_{MH} \cdot \rho_{MH} \cdot c_{AHZ} \cdot \rho_{AHZ} \cdot \left((r + \sqrt{D \cdot t_{heat}})^2 - r^2\right)/r^2} \qquad \text{Equation 7}$$

With the above equation, the temperature to which an (approximately) cylindrical conductor is heated during the heating duration $t_{heat}$ can thus be approximately estimated, in order to preferably be able to determine the parameters for achieving the denaturation temperature. If only a portion of the heating element is taken into consideration (for example because the heating element consists of a complex geometrical series arrangement of conductors), it is obvious that, for the voltage, only the voltage that drops over the respectively considered conductor is relevant.

The first factor $$\frac{U^2 \cdot \sigma}{l^2}$$

in the above equation is thereby the volumetric heating density, which is described as q below, i.e.

$$q = \frac{U^2 \cdot \sigma}{l^2}.$$

This in turn means that the temperature increase in Equation 8 is proportional to the volumetric heating density.

Figure 2A:
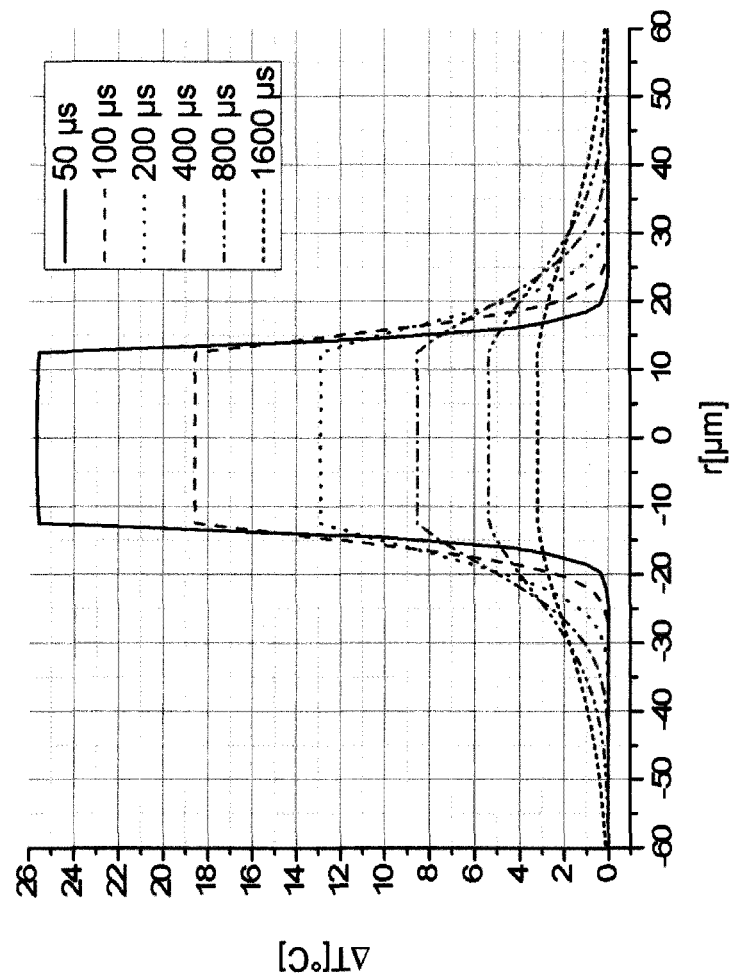
FIG. 2A shows the spatial and time-based progression of the temperature in the cooling phase of a previously heated cylindrical heating element.
Figure 2B:
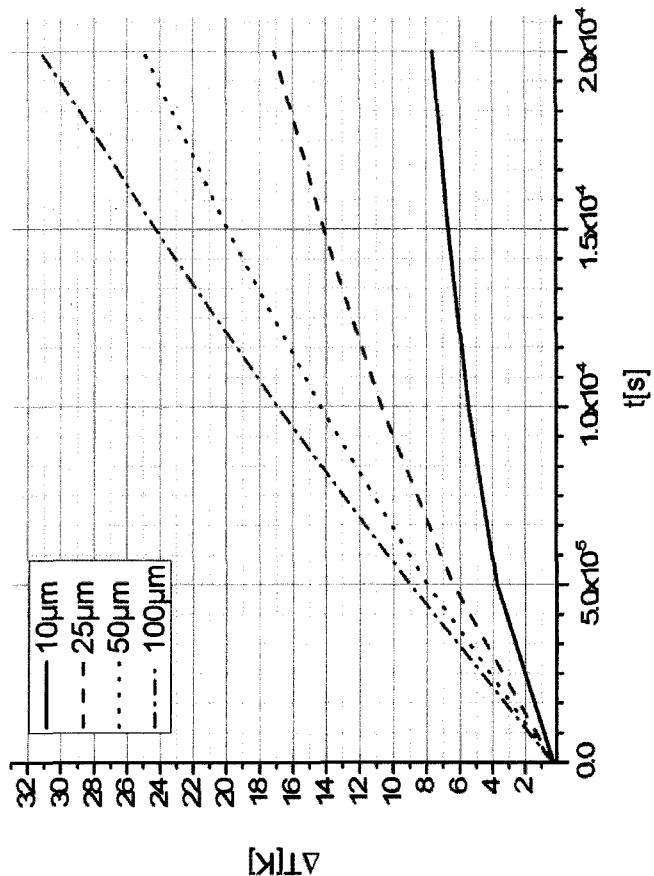
FIG. 2B shows the time-based progression of the surface temperature of cylindrical heating elements of different diameters during heating.

If the heating element(s) is/are for example designed as wires from gold (Au) with a length of the wire l=0.1 m and also a radius of the wire of r=12.5 µm and the material parameters $$\rho_{MH} = \rho_{Au} = 19200 \frac{\text{kg}}{\text{m}^3},$$

$$c_{MH} = c_{Au} = 125 \frac{\text{J}}{\text{kg} \cdot {}^\circ \text{C.}} \text{ and}$$

$$\sigma = \sigma_{Au} = 4.6 \cdot 10^7 \frac{\text{A}}{\text{Vm}},$$

based on a voltage of U=10.5V spacing before V and a heating duration of $t_{heat}$=200 µs according to Equation 7 this results in a local temperature increase on the heating element of $\Delta T_{local} \approx 14.4^\circ$ C. (when using $$\rho_{AHZ} = \rho_{H_2O} = 1000 \frac{\text{kg}}{\text{m}^3},$$

$$c_{AHZ} = c_{H_2O} = 4200 \frac{J}{kg \cdot {}^\circ C.},$$

which are typical values for the reaction volume contained in the heating-up zone). From the operating parameters used, the volumetric power and heating density q can be calculated with $$q = \frac{U^2 \cdot \sigma}{l^2} \approx 5 \cdot 10^{11} \text{ W/m}^3,$$

so that a comparison with the results of the finite element simulations in FIG. 2B is possible. This shows, after 200 µs heating durations for a cylindrical heating wire at the said heating density of $5 \cdot 10^{11}$ W/m$^3$, a heating of just about 17° C.

Provision of the Electrical Power and Energy Density

In a preferred embodiment of the invention, in at least one, preferably in at least three, particularly preferably in at least 10, particularly preferably in at least 20 of the passages of the amplification cycle of the PCR, the average volumetric power density of the heating means is greater than $10^9$ W/m$^3$, preferably greater than $10^{10}$ W/m$^3$, particularly preferably greater than $10^{11}$ W/m$^3$ It is an achievable advantage of this embodiment of the invention that the heating element is heated sufficiently quickly even with short duration of the heat pulse.

In a preferred embodiment of the invention, in at least one, preferably in at least three, particularly preferably in at least 10, particularly preferably in at least 20 of the passages of the amplification cycle of the PCR, the average specific power density of the heating means is preferably less than $10^{16}$ W/m$^3$, particularly preferably less than $10^{15}$ W/m$^3$ and particularly preferably less than $10^{14}$ W/m$^3$. With this embodiment of the invention, damage to the heating elements can advantageously be avoided.

In the case of a heating resistor being used as a heating element, the specific power density q, which is generated in the heating element, is given by $$q = \frac{U^2 \cdot \sigma}{l^2}$$

i.e. a voltage U that is as high as possible, a conductivity σ that is as high as possible and a short length l, over which the voltage drops in the heating element lead to a high specific power density. The entire electrical power requirement resulting for the provision of the heat pulses is thus calculated from the required volumetric power density and the combined volume of all heating elements of the heating means, wherein it depends, inter alia, upon the reaction volume that is to be processed.

Global Heating of the Sample Through the Local Heating Step for the Denaturation In a preferred embodiment of the invention, current pulses through the heating means are selected so that only the heating means and the reaction volume in the direct vicinity of the surface of the heating means are significantly heated, thus a merely local heating takes place. The amount of heat Q brought in in the course of the whole denaturation step is produced locally in the heating means and is distributed initially over the heating means itself and the direct vicinity thereof, as the discharge of the heat through diffusion takes place only gradually, as explained below. This means that the amount of heat Q brought is an amount of energy that is initially distributed over a very small volume and, in time, spreads ("flows") into the surrounding reaction volume. Provided that the amount of heat (often also only described just as the "heat") is still spatially concentrated in the heating element and its direct vicinity, it brings about a substantial temperature increase there. As soon as this amount of heat is distributed over an increasingly large volume, however, it also brings about a temperature increase there, but which is correspondingly smaller, as the originally brought amount of heat naturally remains constant (if only the liquid volume of the reaction volume is considered, the temperature decreases inversely proportionally to the volume, over which the amount of heat is distributed).

It is only after a certain time, hereinafter referred to as the "sample thermalisation time" and defined in the following paragraph, that the amount of heat is distributed to the whole reaction volume and causes a global temperature increase there. Depending on how well insulated the reaction volume is, or how well it is coupled to an external thermic tank, the brought amount of heat can remain in the reaction volume (with very good insulation, which then leads to a gradual, slight increase in the global temperature of the reaction volume with each passage of the amplification cycle of the PCR) or, in the case of good thermic thermal contacting of the reaction volume, the heat flows away, so that the reaction volume goes back to the original temperature (before the heating step). In practice, it is mostly the case that a part of the brought amount of heat flows away in the time between two denaturation steps so that the global temperature of the reaction volume increases slightly (typically less than 3° C.) over the first passages of the amplification cycle of the PCR until an equilibrium state has formed and, for each cycle, the same amount of heat is brought in as the amount of heat that flows away.

The sample thermalisation time is the time until the brought amount of heat has spread from the heating means to the whole reaction volume. The sample thermalisation time can be estimated by initially determining the point(s) at the greatest distance $d_{max}$ from the nearest heating element (typically, in many cases, these points lie on the surfaces that delimit the reaction volume). The sample thermalisation time is then the time taken until the heat diffusion range is equal to $d_{max}$, i.e. in terms of image, until the heat that is generated in the heating elements has diffused into the last "corner" of the reaction volume. If, for example, the reaction volume is cylindrical with a radius of 1.01 mm and the heating element consists of a single cylindrical wire with a radius of 0.01 mm, which runs concentrically through the axis of the cylinder, the maximum distance that a point in the reaction volume can be from the nearest (in this case the only) heating element is $d_{max}$=1 mm. With Equation 1, a heat diffusion range of 1 mm is produced after 6.3 s, so that in this special case the sample thermalisation time is approximately 6.3 s.

The MGTE, which is the maximum increase in the average temperature taking place through the denaturation step, can be estimated as follows from amount of heat Q and the heat capacitance that is brought through the heating step into reaction volume, with $$MGTE \leq \frac{Q}{C}.$$

With the density p of the reaction volume, its volume V, its specific heat capacity c and with the aid of the correlation C=c·p·V it can be estimated that $$MGTE \leq \frac{Q}{c \cdot p \cdot V}.$$

The less-than sign is substantiated in that the heat capacity of the heating means and the reaction container is not taken into consideration here. The density and heat capacity of the reaction volume is generally substantially that of water, i.e. $p=1$ g·cm$^3$ and c=4.2 J·°C.$^{-1}$·g$^{-1}$. The amount of heat Q can be determined from the electrical operating parameters: If the heat pulse $t_{Heat}$ continues and if the voltage U and the current I during the heat pulse are constant, then $Q=U·I·t_{heat}$. (Insofar as current and voltage are changeable over time, the following applies:

$Q=\int_0^{theat}U(t)·I(t)·dt)$.

This means in the first case that the upper limit for the MGTE can be determined by the equation $$MGTE \leq \frac{U·I·t_{heat}}{4.2\ J·cm^{-3}·V}$$ Equation 8

(the volume V is then to be indicated in millilitres). Here, of course, only the voltage U that drops via the heating means in the reaction volume V is to be considered, and also the current I that actually flows through the heating means in the reaction volume V. (This means: the voltage drop in inlet lines would for example not have to be considered.)

The MGTE can be experimentally determined by the temperature of the reaction volume being taken before and after a single denaturation step, wherein in the latter case it is only after the sample thermalisation time that the physical measurement of the temperature in the reaction volume is carried out. The difference between the two measured temperatures is then equal to the MGTE. This procedure is advantageous according to the invention, as a complete thermalisation of the reaction volume, i.e. an even distribution of the heat in the reaction volume is ensured and the temperature sensor does not detect the temperature of the heating-up zone, for example randomly). This measurement of the MGTE can for example in practice be detected with a temperature sensor, preferably with a particularly small heat capacity of its own, which is brought into the reaction volumes.

Example of a Heating Means

FIG. 1A shows in a schematic illustration a heating element forming a heating means, which can be connected to a voltage source 2, wherein a device for generating electrical pulses 3 changes the temporal current pattern 4. Here, the device for generating electrical pulses 3 is a switch, which is open in the state shown, whereby in the temporal/time-based-related current pattern 4, no pulse can be seen. The heating element 1 is functionalised with primers 5, onto which free target nucleic acids 6 can hybridise. On the right-hand side of the drawing, the spatial progression of the temperature distribution in and around the heating element is shown. At the point in time of the open switch the heating element is not heated with respect to the surrounding liquid and the temperature profile is therefore planar.

Figure 1B:
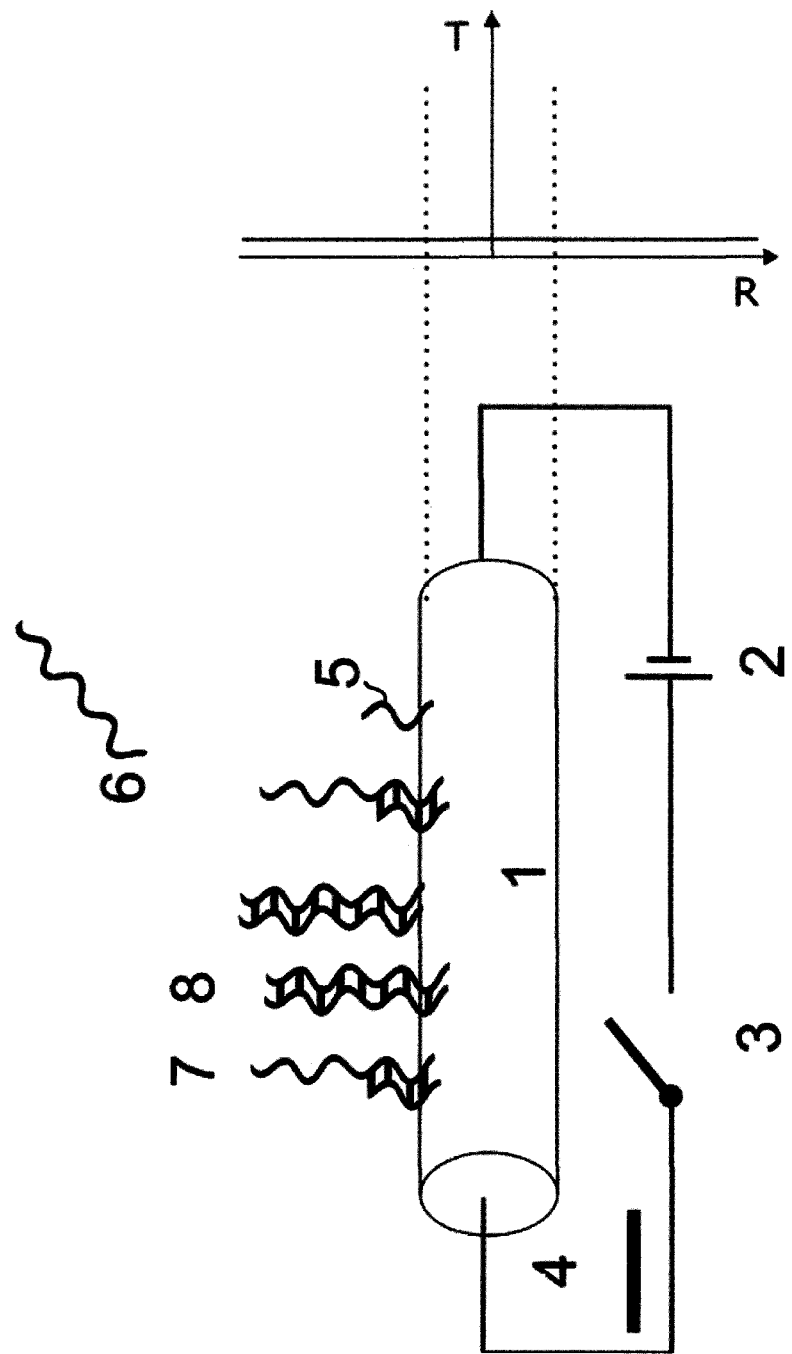
FIG. 1B shows schematically a DNA-functionalised heating element, through which there is no current flow, as the switch is open. Duplexes of primers and target nucleic acid have formed on the heating element and have already partially been elongated.

FIG. 1B shows once again in a schematic illustration the heating element 1. After hybridisation of the primer 5 with the target 6, this primed target nucleic acid 7 can be elongated by the polymerase to form a nucleic acid double strand 8.

Figure 1C:
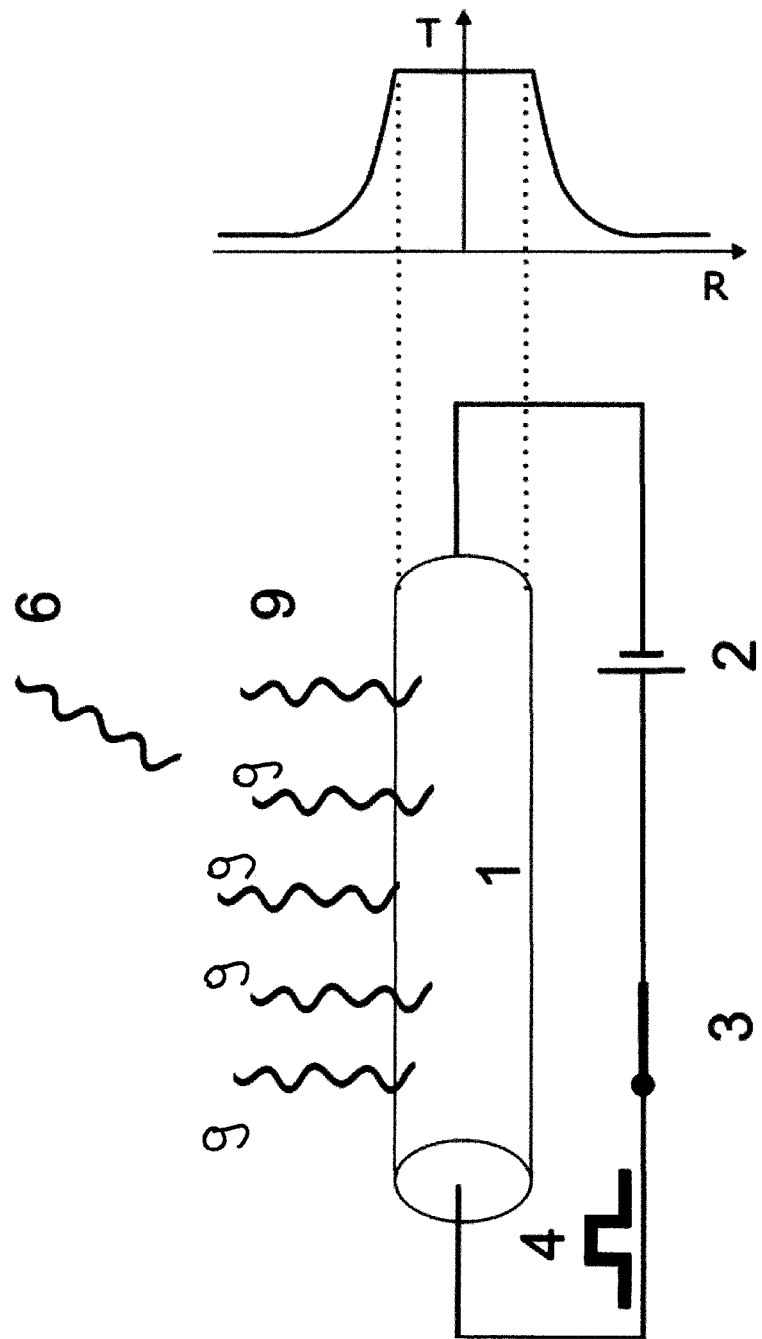
FIG. 1C shows schematically a DNA-functionalised heating element, through which there is a current flow, as the switch is closed. A denaturation of the double strands has taken place on the heating element, with the result that only the elongated primers remain.

FIG. 1 C shows how, after the elongation of the nucleic acid, the device for generating electrical pulses 3 becomes active (the switch shown here is now the closed state), whereby in the temporal current pattern 4 an electrical pulse can be seen. This leads to a heating of the heating element 1 and the local vicinity thereof (shown in the spatial progression of the temperature distribution in and around the heating element on the right hand side of the drawing), whereby, in the case of sufficient local heating, the nucleic acid double strands are denatured and, once again, free targets and amplicons 6 are formed and primers 9 elongated on the heating element remain. Both free targets and amplicons and also the elongated primers can serve in the subsequent amplification cycles as a template for further amplification.

Simulated Temperature Patterns

FIG. 2A shows a finite element simulation for the spatial temperature pattern in a heating wire (which stands for example for a heating element) and the vicinity thereof at different point in times, namely 50, 100, 200, 400, 800 and 1600 μs after the start of a heat pulse. On the vertical axis, the temperature increase is recorded in relation to the value prior to the start of the heat pulse. On the horizontal axis, the distance from the cylinder axis of the wire is recorded. It is assumed here that it is a wire made of gold with a diameter of 25 μm, which is heated for 50 μs with a volumetric power density of 2·10$^{12}$ W/m$^3$ (corresponds according to the equation $$q = \frac{U^2·\sigma}{l^2}$$

to a voltage of 210 V per metre of heating wire length) in an aqueous vicinity.

It can be recognised that after 50 μs a temperature increase of approximately 25.5° C. is reached on the surface of the wire, but the temperature increase already falls already after a few micrometres from the surface. After 1600 μs (i.e. 1550 μs after the end of the heat pulse) on the other hand the heat has already diffused around 10 μm away from the surface of the heating wire and thus fills out a far larger volume. This leads to the temperature on the surface of the wire being only approximately 3° C. warmer than prior to the heat pulse.

It should be pointed out that the curve progression is scaled proportionally to the volumetric power density. This means for example that, for a 4× power density (corresponds to double the voltage with constant wire length) the temperature lift of the whole spatial temperature pattern multiplies by four.

FIG. 2 B shows a finite elements simulation of the time-based temperature pattern on different heating wires (which stand for example for a heating element) since the start of the heat pulse, i.e. the heating-up behaviour of the heating wires is shown. On the vertical axis the temperature increase is recorded with respect to the value before the start of a heat pulse. On the horizontal axis the time since the start of the heat pulse is recorded. It is assumed here that there were full wires made of gold with diameters of 10, 25, 50 and 100 μm, which are heated with a volumetric power density of 5·10$^{11}$ W/m$^3$ (corresponds to a voltage of 104 V per metre of heating wire length). It is to be noted here that the constant volumetric power density leads to the wires with larger diameter being heated with a higher power (as they have a larger volume), which is ultimately due to its lower electrical resistance and thus the higher current flow with constant voltage.

It can be seen that initially (in the first microseconds) the temperature increase on the wire surface increases approximately linearly with the heating duration and then —above all, with small wire diameter—flattens out and increases less than linearly. This effect is due to the fact that, with small diameters of the heating element, the heat capacity of the heating-up zone plays a greater role, or, in other words, that the transport carrying away removal of the heat through diffusion due to the higher volume/surface ratio for small wire diameters is of consequence at an earlier point in time. It should be pointed out that the curve pattern is scaled proportionally to the volumetric power density. This means, for example that, for a 4× fourfold power density (corresponds to double the voltage with constant wire length) the temperature reached on the surface of the wire also increases fourfold.

Figure 2C:
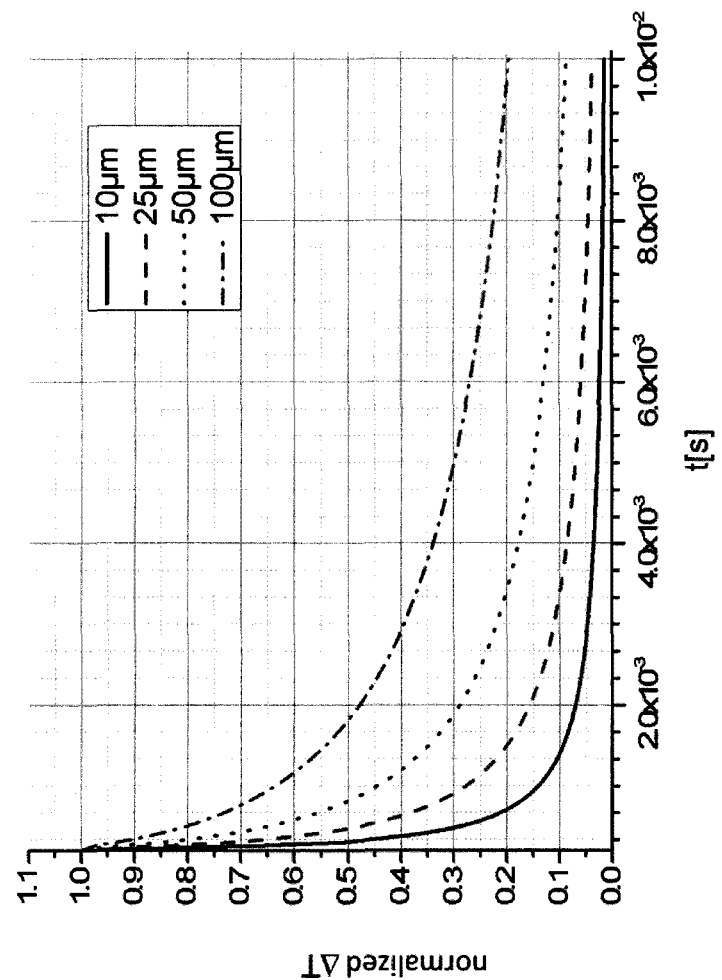
FIG. 2C shows the time-based progression of the surface temperature of cylindrical heating elements of different diameters during cooling.

FIG. 2C shows a finite element simulation of a standardised time-based temperature pattern on different heating wires (which stand for example for a heating element) after the end of a heat pulse with a duration of 200 µs, i.e. the cooling behaviour of the heating wires is shown. On the vertical axis, the still present standardised temperature increase is recorded with respect to the value before the start of the heat pulse. On the horizontal axis, the time since the end of the heat pulse is recorded. It was assumed here that there were full wires made of gold with diameters of 10, 25, 50 and 100 µm, which had been heated for 200 µs. It can be seen that, for all wire diameters, already after 10 ms the original temperature increase (at the end of the heat pulse) has fallen to a fraction. For wire diameters of 10 and 25 µm, the remaining temperature increase has even decreased to less than 5% of its initial value, which shows the potential of the invention, namely in that in the case of a wire of 10 µm diameter, the next heat pulse (i.e. denaturation step or PCR cycle) is possible already after 10 ms. The smaller the wire diameter is, the higher is the surface/volume ratio and the quicker the cooling takes place after the heat pulse.

Figure 2D:
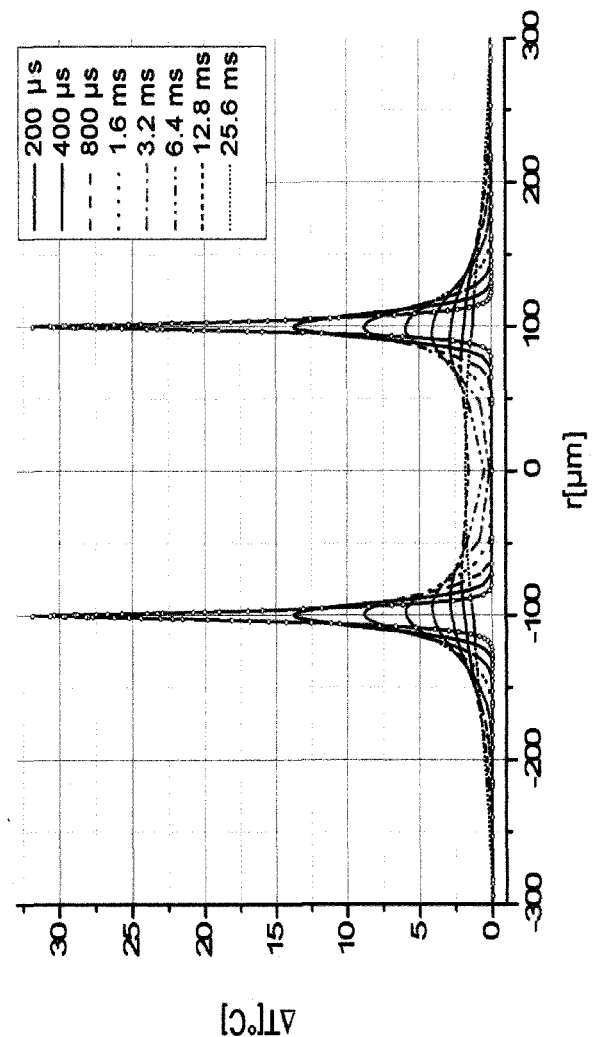
FIG. 2D shows the spatial and time-based progression of the temperature in the cooling phase of a previously heated gold film on an unheated cylindrical carrier.

FIG. 2D shows a finite elements simulation of the temporal temperature pattern of a heating element since the start of the heat pulse, i.e. its heating-up behaviour is shown. The heating element consists of a 200 nm (nanometre) thick gold film, which has been applied to a non-conductive PMMA cylinder with a diameter of 200 µm. On the vertical axis, the temperature increase is recorded with respect to the value before the start of the heat pulse. The values on the horizontal axis indicate, with their amount, the distance from the cylinder axis. It was assumed here that there was a 200 nm thick cylinder sheath made of gold, which is heated with a volumetric power density at the level of $2.2 \cdot 10^{13}$ W/m$^3$ (corresponds to a voltage of 692 V per metre of cylinder sheath length) for the duration of 200 µs, whereas, inside the cylinder (which is made of plastic) in the same way as in the surrounding aqueous reaction volume, no heat is generated (i.e. the volumetric power density there is 0 W/m$^3$. After 200 µs of heating duration the temperature distribution (in the radial direction) is still strongly localised around the gold film and the heat cannot spread in the shortness of time in the aqueous outer region or in the middle of the cylinder. After the end of the pulse (t>200 µs) the gold film cools and the heat spreads into the aqueous outer region and the inside of the cylinder. After approximately 6.4 ms it can be seen that the thermal fields generated in the cylinder sheath run together in the middle of the cylinder so that, here, the temperature initially increases in the further progression. In the outer region on the other hand it can be seen that, already after 25 ms, the temperature increase is only less than 2° C. Two advantages of the use according to the invention of thin metallic films as a heating element can be seen here, namely that they can be applied on a large surface (here a cylinder with a diameter of 200 µm) and at the same time have a very small volume (and thus thermic mass), so that they cool out again almost completely in very short times («1 s).

Experimental Conversion

Figure 3A:
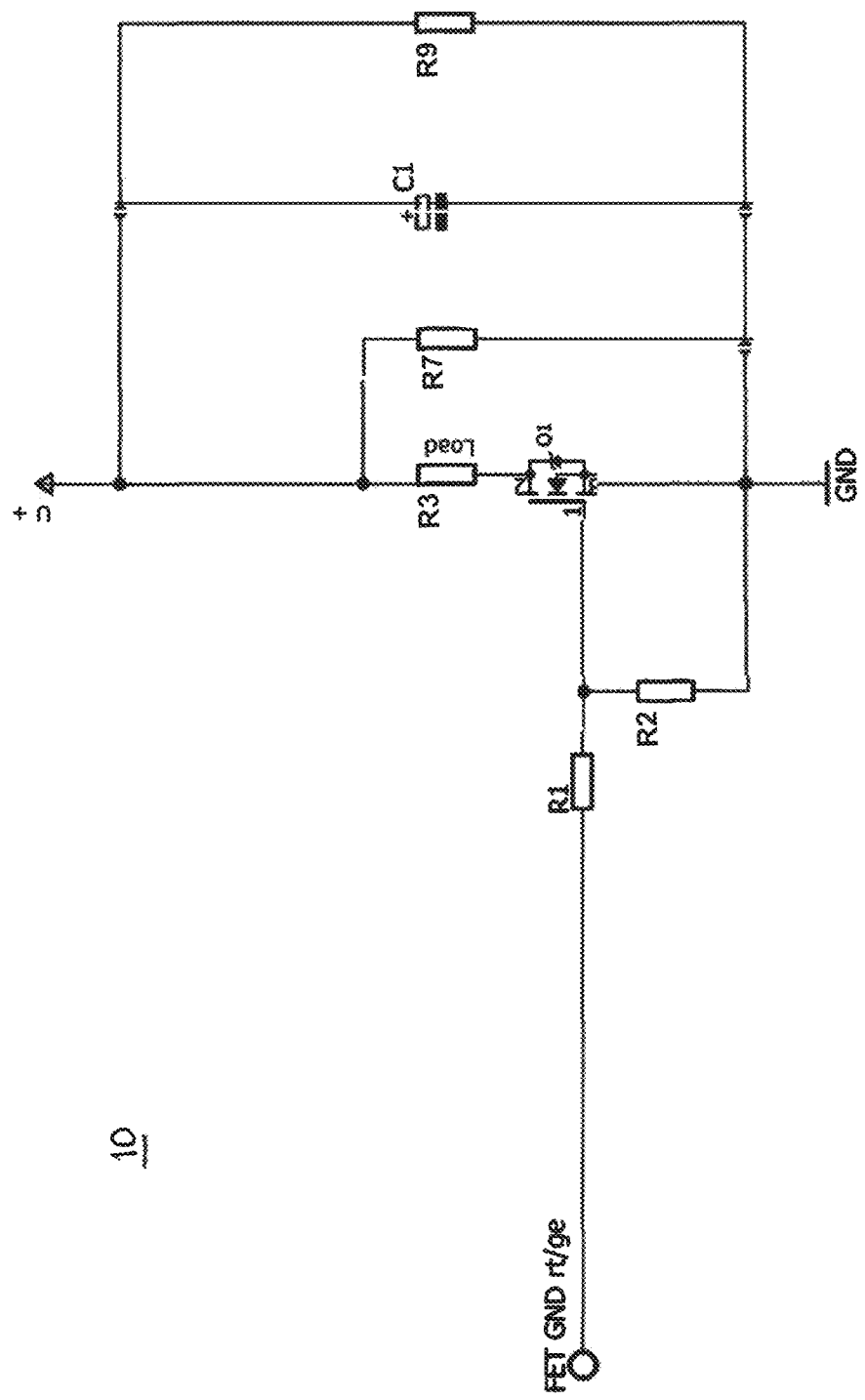
FIG. 3A shows an electronic circuit for generating current pulses.

FIG. 3A shows the example of an electrical circuit 10 as a control device for generating electrical pulses in order to apply electrical current to the heating means. The circuit is constructed so that between earth (GND) and U+, a voltage (in this document always indicated as "U") is supplied (for example between 30 and 100 V), with which the heating means is to be heated. At the point R3 "Load", the heating means is arranged, so that R3 is the resistor of the heating means. The power MOSFET Q (IRFP4468, International Rectifier), used by way of example, produces a low ohmic connection between the contact T2 and contact T3, in the connected-through, in such a way that a current flows through the heating means R3. Between earth and the gate (contact T1) of the MOSFET, a control voltage, which is provided for example by a pulse or frequency generator or a digital-analog converter, is supplied via the control terminal FET GND rt/ge. Particularly suited are pulses with a level of 5 V and a duration of for example between 10 and 1000 µs, which allow a clean connection of the MOSFET. At the point C1, a capacitor with sufficient capacitance, example 4 mF, and lowest possible ESR value is provided, which allows, even with low ohmic heating means—resistance of all heating elements together typically less than 1Ω (Ohm)—the supplied voltage to be maintained for the duration of the heat pulse. The resistors R1, R2, R7 and R9, for example, have resistance values of 1, 100, 24 and 24 kΩ(kiloohm).

FIG. 3B shows schematically and in a simplified manner the cross-section of an embodiment of the invention, wherein the heating means is formed by portions of a continuous wire 12, which is connected to a voltage source 11. To simplify the illustration, the device for generating electrical pulses has been omitted. In addition and the drawing is not true to scale. The wire runs through a plurality of reaction vessels, separate from each other, in the form of sample liquid chambers (also known as "wells") in a sample plate 13, which is located between a two-part temperature-regulating block 14. The temperature-regulating block 14 has the function of bringing the reaction volume in the sample liquid chambers to hybridisation/elongation temperature and holding it there. In the embodiment here, in the lower part of the temperature-regulating block 14 below each sample liquid chamber, there is an excitation light source (in this case in the form of a light emitting diode 15 with an optical low pass filter) for exciting a dye in the respective reaction volume, and, in the upper part of the temperature-regulating block 14 over/above each sample liquid chamber, there is a photodiode 16 as a light sensor for detecting the fluorescence of the excited dye in the respective reaction volume (with an optical high pass filter, which allows fluorescent light to pass through).

FIG. 3C shows schematically and in a simplified manner the cross-section of a further embodiment of the invention, which differs from the exemplary embodiment of FIG. 3B in that the heating elements are designed as coils composed of a wire 12 connected to a voltage source 11. To simplify the illustration, the device for generating pulses has also been omitted here. The heating elements in the form of wire wound up into coils are in contact with the reaction volume in the respective reaction vessel. Contrary to how they are shown in the figure, they are preferably completely surrounded by the reaction volume. The reaction vessels in this exemplary embodiment are a plurality of sample liquid chambers, separated from each other, in the form of reaction tubes, which are located in a temperature-regulating block 14 in order to bring the reaction volumes to hybridisation/elongation temperature and to keep them there. In the embodiment shown here, in the lower part of the temperature-regulating block 14 below each sample liquid chamber, there is a light emitting diode 15 as an excitation light source for exciting a dye in the reaction volume, and, above each sample liquid chamber, there is a photodiode 16 as a light sensor for detecting the fluorescence of the excited dye in the reaction volume.

Production of a Sample Plate with Wire Heating Elements

FIG. 3D shows schematically components, from which a sample plate of a device according to the invention can be created with wire heating elements. The heating elements used here are portions of a gold-plated sheathed wire 12 of 25 µm in diameter (23 µm tungsten core with approximately 1 µm gold sheath, LUMA METALL AB, Kalmar, Sweden). This is wound around an acrylic glass plate 17 having a thickness of 0.5 mm (middle, lighter plate). In the plate there are seven openings (6 mm×6 mm), through which the sample liquid chambers (wells) are defined. Through the winding, there are two parallel layers in each sample liquid chamber, each layer having fifteen parallel heating elements; the two layers of the heating means are at a distance of 0.5 mm due to the plate, the heating elements within a layer have a distance of approximately 0.4 mm. From both sides, by means of doubled-sided adhesive foils 18 (shown darkened, 100-250 µm thick VHB adhesive tape of 3M) with corresponding receptacles for the sample liquid chambers, a further acrylic glass plate 19 (thickness of the lower plate 0.5 mm and thickness of the upper plate 3 mm) with equal openings is stuck to the plate 17, and pressed according to the manufacturer's indications of the adhesive tape 18. From below, the wells are each closed with a thin foil 20 (lighter in the illustration, adhesive PCR foil seal, 4titute), which are stuck to the bottom acrylic glass plate. In this way a sample plate with seven wells is formed, through which parallel wires 12 can be pulled. The wires 12 are connected to each other at the two outer-lying ends of the plate (i.e. all wires/heating element are connected in parallel) and in electrical contact. It is made possible in this way for current pulses to be sent in series through all the wells. The openings of the sample plate (at the top here) can then be closed with a thin foil 21 (shown in a light colour). The sample plates have a width of 20 mm and a length of 90 mm (so that the voltage of the heat pulses drops essentially over a length of approximately 96 mm if the 3 mm overhang of the wires at the ends are considered, which are required for contacting purposes).

Measuring the Global Temperature Increase

Figure 3E:
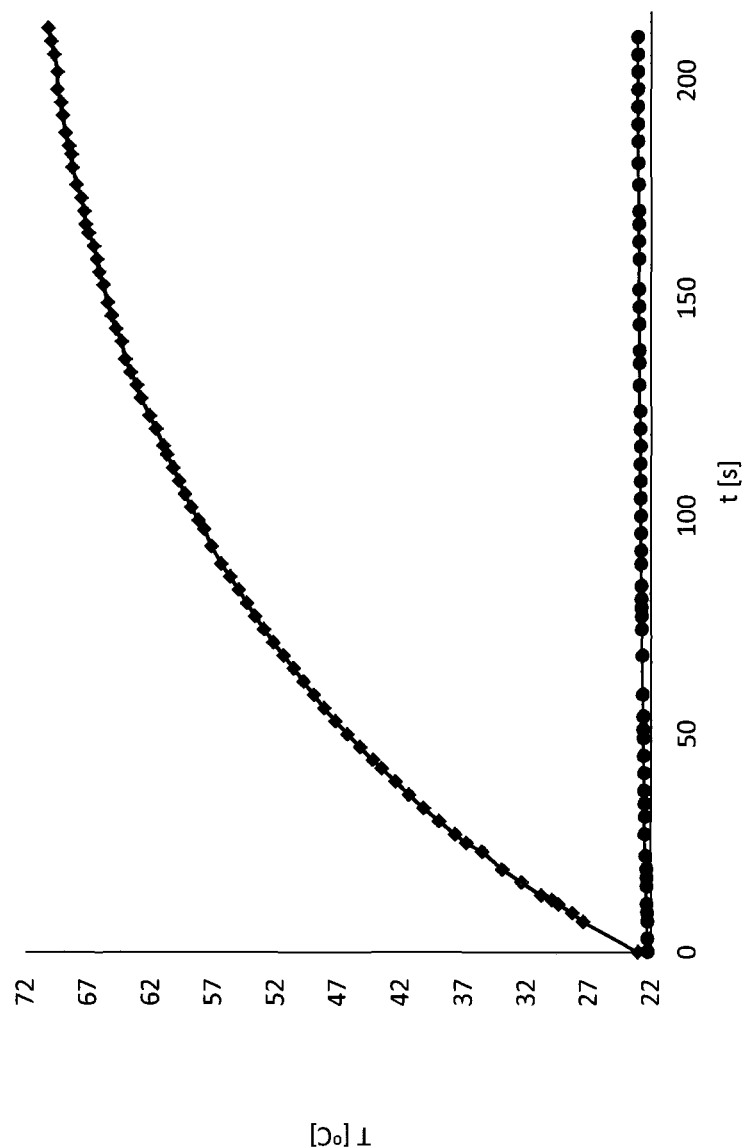
FIG. 3E shows the global temperature increase in aqueous solution with different current flows, i.e. heating of the heating elements.

FIG. 3E shows the result of a measurement of the global temperature increase in a reaction volume of an exemplary embodiment of the invention according to FIG. 3D.

The wells of a sample plate produced as described in FIG. 3D are each filled with 100 µl of water. A PT100 sensor as a temperature sensor is additionally inserted into one of the middle wells. If a constant current of 3 A is sent through the wires, a temperature increase of approximately 47° C. is observed over a time of 200 s in the water sample (curve with hashes). If on the other hand, as provided according to the invention, current pulses of 80 A are sent with 70 µs duration through the wires every 3 s (voltage 32 V supplied, load resistance the wires, 0.4Ω), merely a global temperature increase of the water sample of less than 1° C. can be measured with this measurement method (curve with circles).

PCR with Genomic Nucleic Acid and Background

Figure 4:
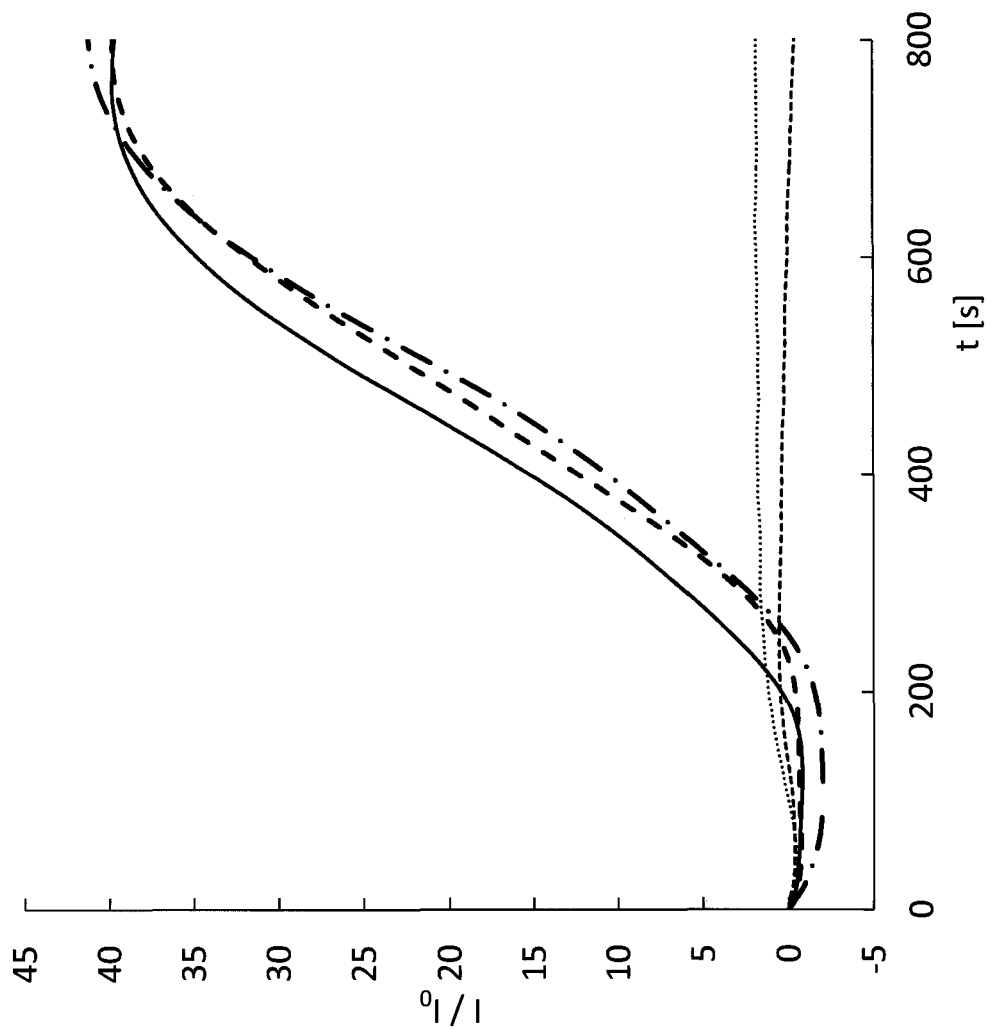
FIG. 4 shows a real-time PCR with local heating with genomic template.

FIG. 4 shows the results of polymerase chain reactions with genomic nucleic acid and control measurements, respectively in a reaction volume of an exemplary embodiment of the invention according to FIG. 3D. The heating elements in the wells of a sample plate produced as described in FIG. 3D are functionalised with forward primers. For the functionalisation, the forward primer ID1 is used. Thiol serves for bonding to the gold surface, the first five thymine bases serve as a spacer sequence in order to obtain more space, or distance, between an actual primer sequence and gold surface and thus to prevent for example possible steric obstacles hindrances. Prior to functionalisation, the protecting group of the thiol modification of the thus formed oligonucleotide is de-protected by the oligonucleotide being incubated in a concentration of 0.5 µm in PBS buffer (5 mM phosphate buffer, 10 mM NaCl, 0.01% Tween20, 1 mM EDTA, pH 7.5) for 15 min. with 1 mM tris-(2-carboxyethyl) phosphine is incubated. Subsequently NaCl (5M) is to be added in order to reach a final concentration of NaCl of 500 mM for the functionalisation. After 3 hours of incubation of the wires with a suspension of the de-protected oligonucleotides, 2 washing steps with PBS buffer are carried out, in order to remove excess non-bonded oligonucleotides. The plates prepared in this way are now available for the amplification reaction.

The amplification reaction was carried out in 90 µl total volume per well. The reaction mix consists of 36 µL, $H_2O$; 9 µL $MgCl_2$ 120 mM; 18 µl 5× Aptataq genotyping master (Roche); 9 µl reverse primer ID2 5 µm; 9 µL TaqMan probe, oligo ID3 2 µm. Added to this, is 9 µl sample, which, depending on the well, contains either boiled genomic nucleic acid or only water. Forward and reverse primers and also the TaqMan probe were selected so that the resistance gene MecA is amplified and detected, whereby this arises for example in the genome of the methicillin resistant *Staphylococcus aureus* (MRSA).

The plate is placed between two temperature-regulating blocks made of aluminium, the temperature of the lower block is 65° C. and the temperature of the upper block is 70° C. The temperature difference serves for avoiding condensate formation on the upper covering foil. The heating means comprising the heating elements is arranged corresponding to FIG. 3A at the position R3 of the circuit, which is operated here with a voltage of U+=32 V. The wires form a load resistance of 0.4Ω, through which, during the following PCR, electrical pulses with the length of 70 µs are sent every 3 s.

For the real-time detection in TaqMan format, there are excitation light emitting diodes in the lower temperature-regulating block, with a corresponding bandpass filter with 478 nm central wavelength and FWHM of 29 nm (ET480/30×, Chroma Inc, USA) and, also in the upper temperature-regulating block, photodiodes and optical filters with a passage area of 515-700 nm (ET510lp, Chroma Inc. USA).

The result of the above-described PCR can be seen in FIG. 4, where the percentage change of the fluorescence signal I during the PCR process (with respect to the fluorescence base signal $I_0$ at the start of the PCR) is shown. In the first well, $10^6$ copies of genomic nucleic acid isolated from MRSA were used as a sample. As this genomic nucleic acid contains the MecA gene and thus the target sequence of the PCR, the corresponding fluorescence curve (solid curve) increases after approximately 190 s PCR duration, as at this time a sufficiently large amount of amplicon has formed (and thus, through exonuclease activity of the polymerase, a sufficiently large amount of FAM dye has been released from the TaqMan probe), in order to generate a signal that can be differentiated from the base fluorescence. In the second well, 100× less target nucleic acid from the same organism was used, the corresponding fluorescence curve (roughly broken curve) increases later here, from 220 s PCR duration onwards. The method thus allows (as is usual in the qPCR) a correlation between target concentrations used and the time of the increase of the fluorescence curve. In the third well, in addition to the reaction mix, only water was added as a negative control (finely broken curve), in the fourth well $10^6$ copies of genomic nucleic acid isolated from *Escherichia coli* (*E. coli*, of which the genome does not contain the MecA gene) was used as a sample in order to demonstrate the specificity of the PCR (dotted line). Neither of the fluorescence curves (water: finely broken line, *E. coli*: dotted line) shows a significant increase. In the fifth well, finally, both $10^4$ copies of genomic nucleic acid isolated from MRSA and also $10^4$ copies of genomic nucleic acid isolated from *E. coli* were used as samples. The corresponding fluorescence curve (dashed-dotted curve) behaves like the fluorescence curve of the sample from the second well, which contains only $10^4$ copies of genomic nucleic acid isolated from MRSA. This shows that the presence of *E. coli* nucleic acid does not supress the amplification of the MRSA nucleic acid. In addition, in a comparable amplification experiment, an external quantification of the amplicon amount produced was carried out with the aid of a conventional thermocycler (Roche Lightcycler 1.5). For this, the above-described PCR process was interrupted shortly after recognisable increase in the fluorescence curve, the sample was removed, 1:100 diluted with water and 1 µl of this diluted sample was inserted into a qPCR, which uses the same primer sequences (forward primer here but without thiol and 5T spacer sequence), as in the case of the PCR described above. The comparison with a dilution series sequence of known target concentrations led to the result that at the point in time of the clear signal increase, there was an amplicon concentration of approximately 3 nM (nanomolar, or nanomol per litre) in the reaction. This is also a typical area for the signal that can be differentiated, fluorescence base all in the case of other thermocyclers, and this additionally clearly shows that during the PCR carried out, the desired amplicon was produced in very large amount. The comparison with FIG. 3E shows that, under the given conditions (supplied voltage 32 V, load resistance of wires 0.4Ω), only a global temperature increase of the reaction volume of <1° C. can be detected within 200 s can be detected, and, therefore, reaching the denaturation temperature (approximately 95° C.) of the reaction volume can be ruled out. Through the functionalisation with thiol-modified forward primer, however, the amplicon is still bonded to a heating element. Obviously, the temperature there locally during the heating steps and during the electrical pulses is sufficiently high in order to achieve a denaturation of the amplicon. (Not shown here: If free unmodified forward primers with sequence ID4, which are added to the reaction mix but do not bond to the wires, are used instead of the thiol-modified forward primers, but under otherwise identical conditions, no amplification can be observed. The amplification reaction is thus, in the case of local heating, preferably localised on a locally heating element, whereby the forward primer is immobilised on the heating element).

Measurements in the Case of Different Volumetric Power Densities

Figure 5C:
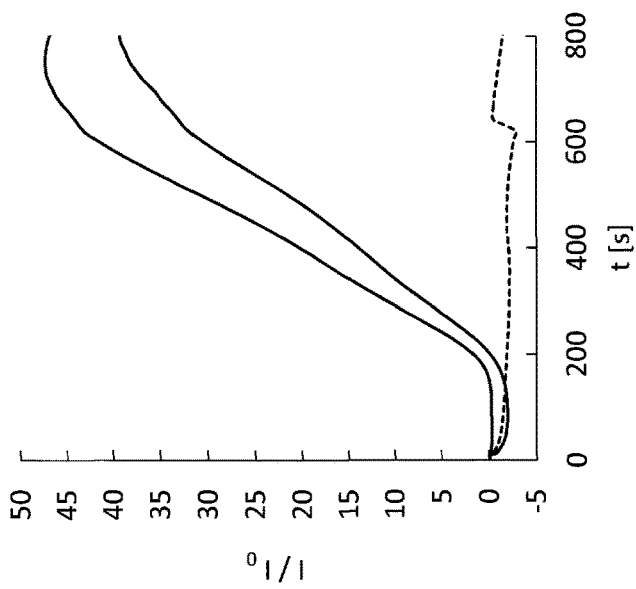
FIGS. 5A, 5B, 5C show a real-time PCR with local heating with genomic template with the use of different voltages for operation of the heating means.
Figure 5B:
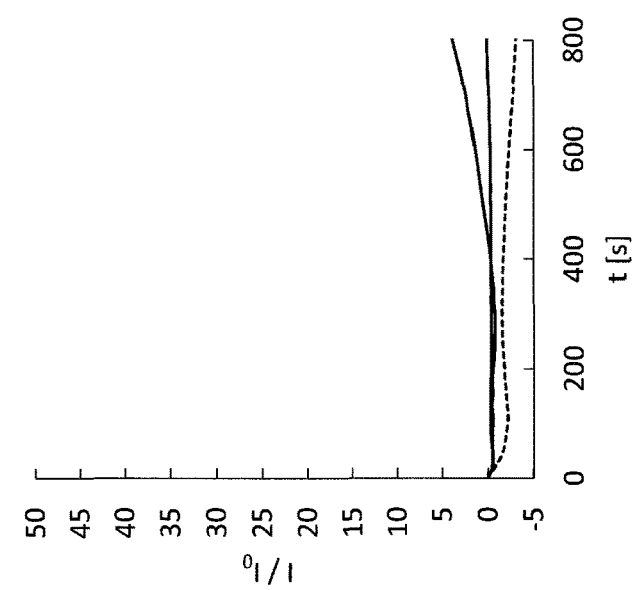
Figure 5A:
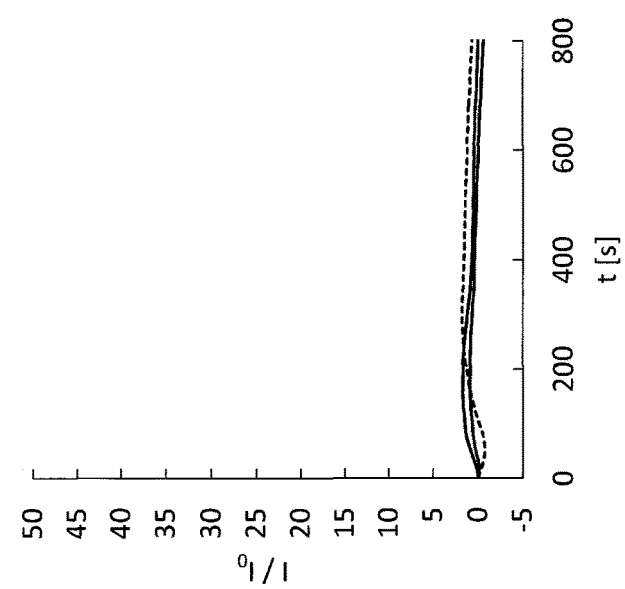
Figure 5E:
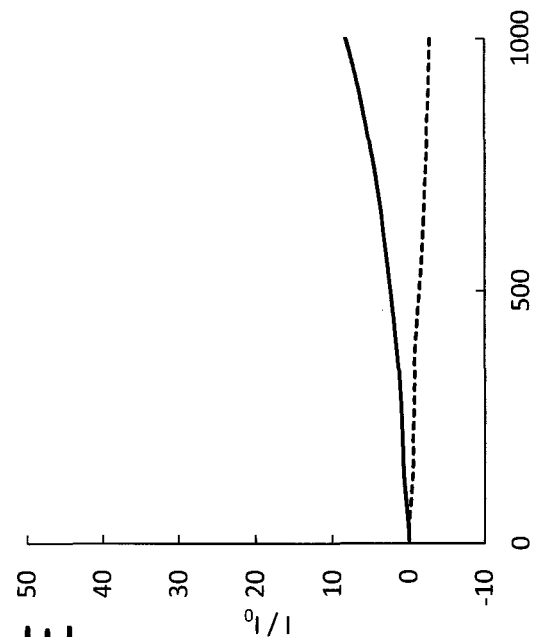
FIGS. 5D, 5E, 5F, 5G show a real-time PCR with local heating with genomic template with the use of many different heating elements.

FIGS. 5A to 5C show, with the aid of exemplary embodiments of the invention, the dependence of the PCR performance upon the supplied voltage, which changes the volumetric heating density according to the equation $$q = \frac{U^2 \cdot \sigma}{l^2}.$$

Here, a measurement series with different voltages supplied to the heating means was carried out. The parameters and reaction mix compositions are identical to those in the exemplary embodiment of FIG. 4, whereby merely by way of sample in a well, water was used as a negative control (broken fluorescence curve) and also, in two wells, a synthetic target nucleic acid with the sequence ID5 was used, so that the final concentration at the start of the reaction was respectively 100 fM (Femtomolar or Femtomol per litre) of the target nucleic acid (positive controls with solid fluorescence curves). The target nucleic acid is the cut-out from the MecA gene, which can be amplified by the selected primer pair. In the first measurement (fluorescence curves in FIG. 5A) the supplied voltage is 26 V and hardly any signal lift can be seen. In the second measurement (fluorescence curves in FIG. 5B) the supplied voltage is 28 V, the positive controls here show a weak, flatly increasing, late arising signal. In the third measurement (fluorescence curves in FIG. 5C) the voltage is 36 V, the two positive controls here increase clearly and sharply steeply with effect from approximately 180 s PCR duration, the negative control does not thereby show a signal. This measurement series shows that the heat brought by the heating means into the reaction volume must be sufficiently great in order to reach the required denaturation temperature of the amplicon locally on the heating elements.

Figure 5G:
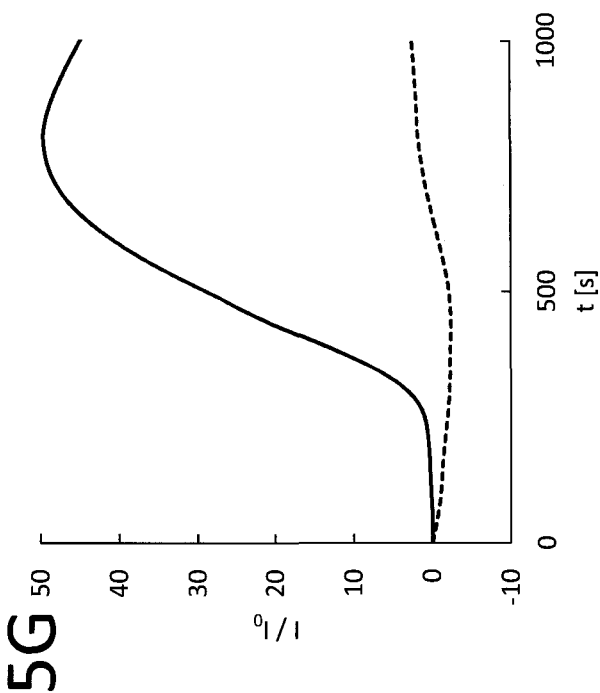
Figure 5D:
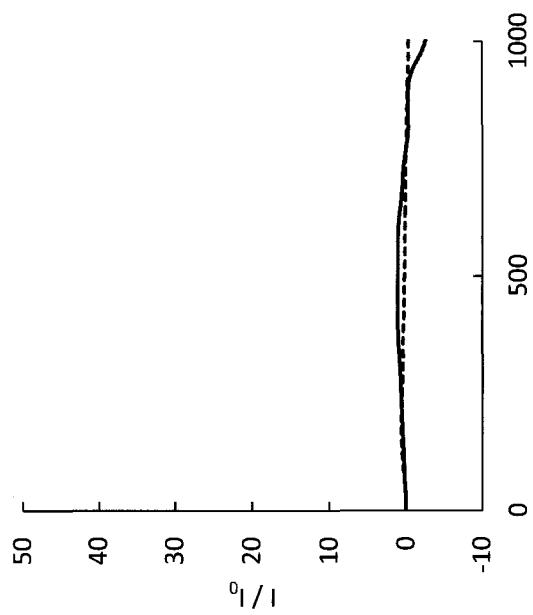
Figure 5F:
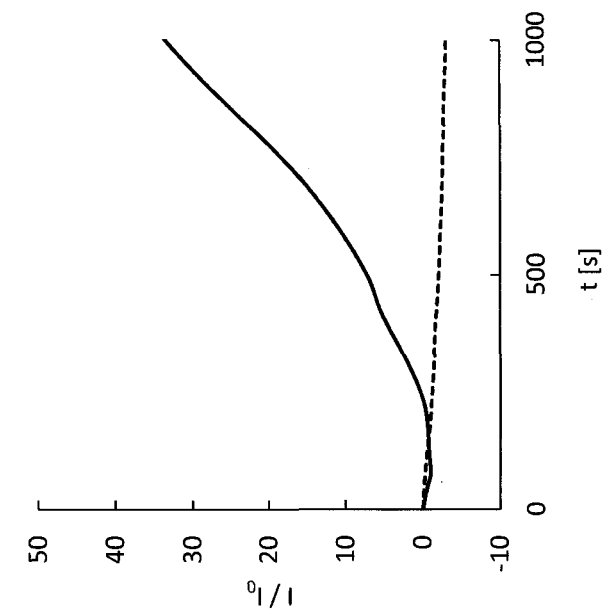

FIGS. 5D to 5G show the results of a series of measurements, in which the sample plates were produced precisely in the manner as set out above in the description of FIG. 3D. However, in each sample plate, a different number of wires was used. In FIG. 5D, 3 wires were used, in FIG. 5E, 5 wires were used, in FIG. 5F, 10 wires were used and, in FIG. 5G, 30 wires were used (connected in parallel over the length of the sample plate: resistances of 3700, 2100, 2210 and 400 mΩ (milliohms). To carry out the PCR, corresponding chemicals and buffers were used as in the text section relating to FIG. 4. To generate the heat pulses, one of voltage U+=40 V, a pulse duration of 40 µs and a pulse repetition rate (i.e. PCR cycle duration) of 3 s was used. The temperature of the lower temperature-regulating block was brought at to 63° C. and that of the upper block at 68° C. By way of target nucleic acid, synthetic DNA ID5 was used, which was present at the start of the reaction in a concentration of 1 fM (solid line). No target was used in the negative controls (broken line). It can be seen that, when using only three wires in the sample plate (first measurement, fluorescence curves in FIG. 5D), even in the positive control, no signal lift (i.e. no TaqMan signal, i.e. no amplification) can be seen. In the case of five wires in the sample plate (FIG. 5E), the positive control exhibits a weak signal. In the case of ten wires in the sample plate (FIG. 5F), the signal is significantly higher, but still significantly weaker than in the fourth measurement, where a usual number of wires (namely 30 is used (FIG. 5G).

Heating Means with Honeycomb Structure

Figures 6A, 6B:
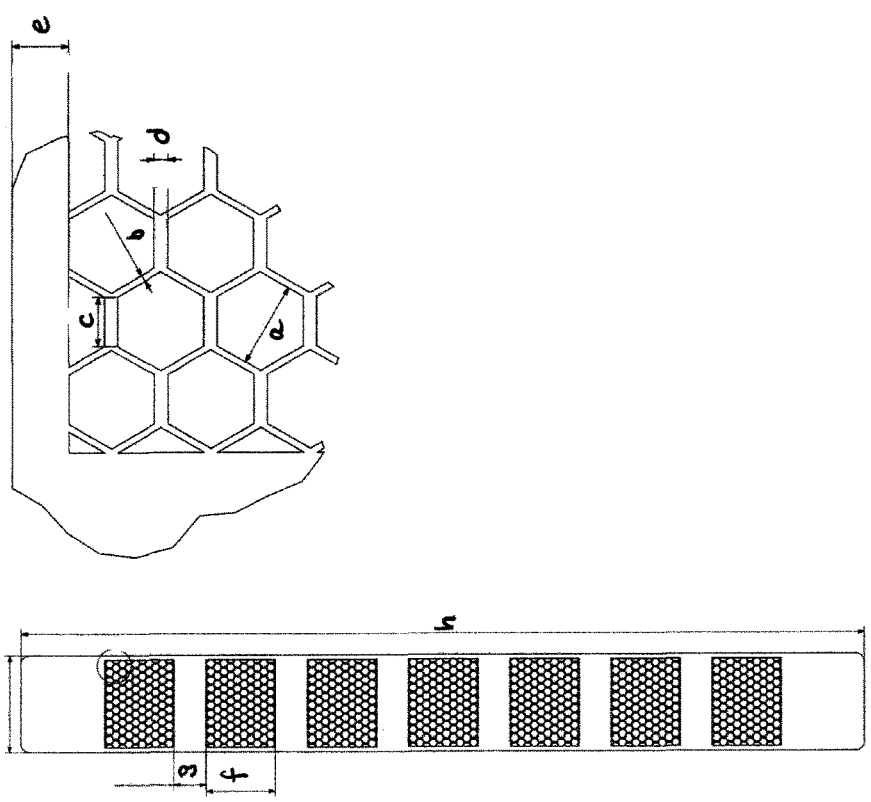
FIG. 6A shows a honeycomb structure that can be electrically heated.
FIG. 6B shows details of the honeycomb structure that can be electrically heated.
Figure 6C:
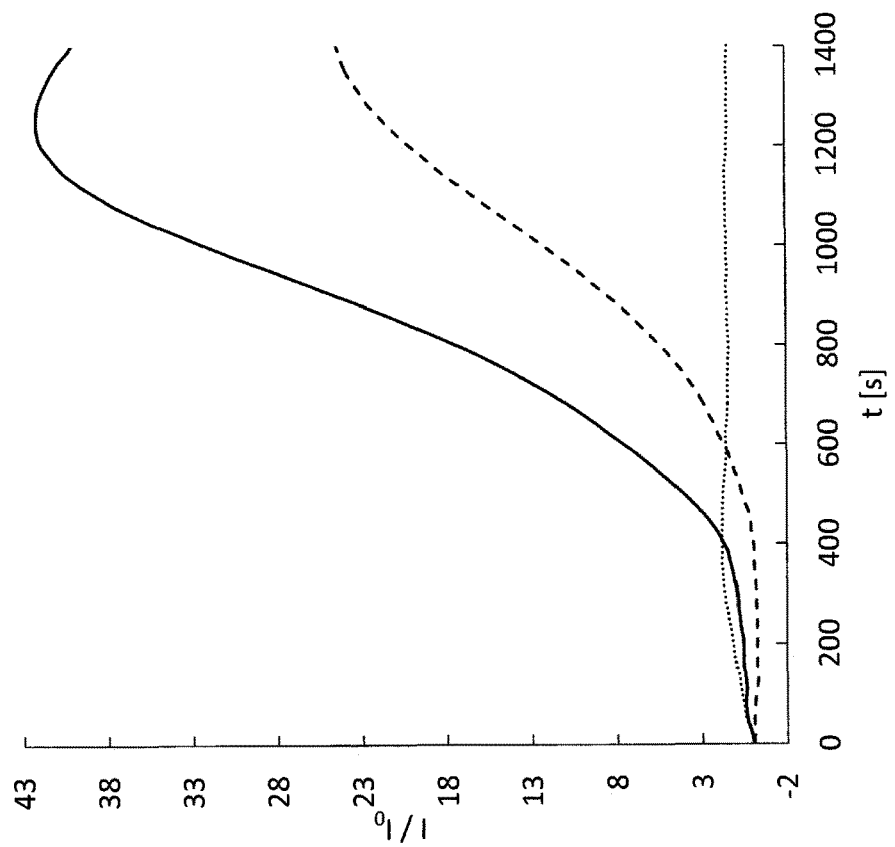
FIG. 6C shows a real-time PCR with local heating with genomic template with the use of the honeycomb structure for local heating.

FIGS. 6A to 6C show an embodiment of the heating means in honeycomb structure.

For the production thereof, a honeycomb structure is produced through photochemical fine etching methods from a stainless steel foil, and subsequently the honeycomb structure is coated with gold. In the exemplary embodiment, it is a hexagonal lattice, but naturally other lattices are also conceivable. The current flows through the structure along the length thereof xx, wherein, as shown in FIG. 6A, only in the area of the sample chambers, thus where the foil forms the heating elements, was a honeycomb structure etched. The length f of a heating element is for example 8.2 mm, the distance g between the heating elements is for example 3.8 mm. The sample chambers are preferably arranged centrally above the heating elements and preferably have smaller dimensions (for example 6 mm×6 mm) in order to use only the area of the heating elements, which is tempered as evenly as possible. The whole length h of the foil is for example 100 mm, i.e. the electrical contacting takes place at the short sides, so that the voltage drops over a length of approximately 100 mm. The webs of the honeycomb structure heat up due to the current passing through them and can denature the double-stranded nucleic acid bonded to them.

FIG. 6B is an enlarged illustration of the honeycomb structure of a heating element of FIG. 6A with adjacent edge. In the example honeycomb structure, the web widths are configured so that overall in the honeycomb structure a current density that is as even as possible and thus volumetric heating density is achieved. In the exemplary embodiment this is achieved in that the width d of the longitudinal webs is precisely double the width b of the transverse webs. Examples for the dimensions are 0.87 mm for the honeycomb diameter a, 0.065 mm for the width b of the transverse webs, 0.5 mm for the web length c, 0.13 mm for the width of the longitudinal webs d and 0.57 mm for the width of a long edge 3. The long edge a serves, above all, for the mechanical stability and experiences a different current density than the honeycomb structure.

FIG. 6c shows, as in FIG. 4, the percentage change of the fluorescence signal I during the PCR process (with respect to the fluorescence base signal $I_0$ at the start of the PCR), wherein now, in contrast with the example of FIG. 4, the heating element used is a stainless steel foil coated with approximately 0.5 µm gold (foil thickness 20 µm) was used with the structure shown in FIGS. 6A and 6B. This gold-plated lattice is stuck between two acrylic glass plates with seven well openings, as were also used for the exemplary embodiment in FIG. 3D (thickness of the lower plate 0.5 mm and thickness of the upper plate 3 mm). There is thus also here, as already in the exemplary embodiment in FIG. 3D, a sample plate, which is traversed by the heating means. The honeycomb structures are electrically contacted at the two outer-lying ends of the plate. It is thereby made possible for current pulses to be sent in series through all wells. The openings of the sample plate can subsequently be closed with a thin foil. The functionalisation of the honeycomb structures is realised similarly to that of the tungsten-gold sheathed wires of FIGS. 3D and 4. The reaction volume is now 60 µl per well, the composition and concentrations of the reaction mix correspond to those of FIG. 4. The voltage supplied is 41 V with load resistance of 0.35Ω. Here, electrical pulses with the duration of 150 µs were sent through the heating elements during the PCR every 10 s. As stainless steel is a significantly poorer current conductor than tungsten, from which the core of the sheathed wire is made in the previous examples, when using heating elements of stainless steel in this example, both a higher voltage and also a longer heating duration are used. In FIG. 6C, the fluorescence curves from three wells can be seen. The negative control with water as a sample does not show a signal increase (dotted fluorescence curve), the sample with a high initial concentration (100 fM) of synthetic nucleic acid target with the sequence ID5 shows an increase of the fluorescence signal with effect from 400 s PCR duration (solid fluorescence curve) and the sample with a lower starting concentration (1 fM) of synthetic nucleic acid target with the sequence ID5 shows a later increase of the fluorescence signal (broken fluorescence curve).

Bridge PCR

Figure 7:
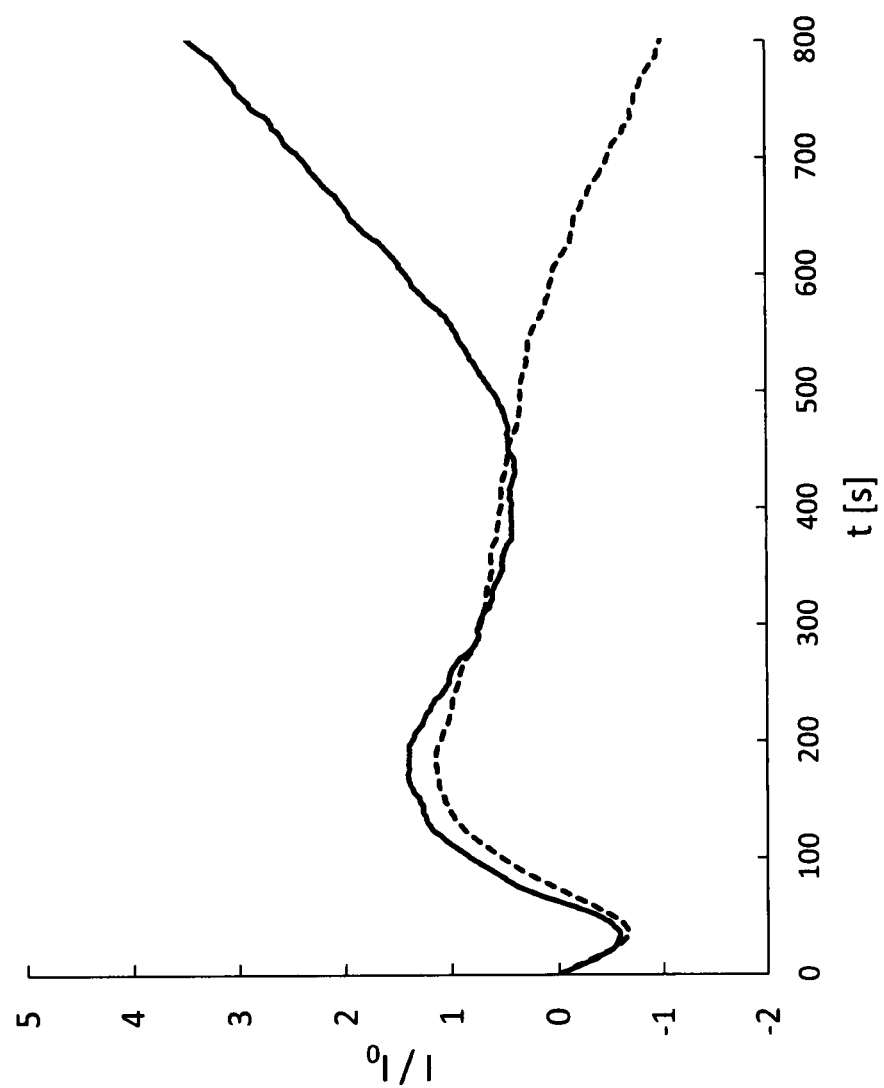
FIG. 7 shows a real-time PCR with local heating and heating element, on which both forward and also reverse primers are functionalised.

In the exemplary embodiment of FIG. 7, both primers (forward primer and reverse primer) are on the surface of the heating means. The procedure for this exemplary embodiment corresponds essentially to that for the exemplary embodiment of FIG. 4.

For the functionalisation of the heating means, however, a mixture of one part of forward primer ID6 and three parts of reverse primer ID7 was used (total concentration of the two primers during the de-protection 0.5 µm). Both primers carry a thiol modification, which serves for immobilisation on the surface of the heating means. The forward primer carries, in addition to a spacer sequence, also two abasic modifications spacer 9 between spacer sequence and primer sequence, which prevents the overwriting of the spacer sequence by the polymerase. As the reverse primer is already present on the heating element, it no longer needs to be present in the reaction volume; the correspondingly missing volume is replaced there by water. The fluorescence curves in FIG. 7 who the signal pattern progression for a negative sample with water (broken line) and a positive sample with a starting concentration of 100 fM of synthetic nucleic acid target with the sequence ID5 (solid line). Indeed the fluorescence signals here are significantly smaller than in the preceding exemplary embodiments, but with effect from 450 s PCR duration onwards, it can also be clearly seen here that the signal of the positive sample increases in comparison with the negative sample. This exemplary embodiment illustrates that a PCR process, of which the primers are both fixed on a surface ("Bridge PCR", see Kawashima et al., WO 1998/044151 A1 and Adams et al., U.S. Pat. No. 5,641,658 A) functions in the method according to the invention.

The features disclosed in the above description, the claims and the drawings, can be of importance both individually and also in any desired combination for the realisation of the invention in its different embodiments.

LIST OF REFERENCE SYMBOLS

1 Wire-form heating element of the heating means
2 Voltage source
3 Device for generating electrical pulses
4 Illustration of the time-based current progression
5 Primer
6 Free target nucleic acid
7 Target nucleic acid bonded to a primer
8 Nucleic acid double strand
9 Elongated primer
10 Electrical circuit
GND Earth connection of the electrical circuit
U+ Voltage supply connection of the electrical circuit
Q1 MOSFET of the electrical circuit
T1 Gate terminal of the MOSFET Q1
T2 Drain terminal of the MOSFET Q1
T3 Source terminal of the MOSFET Q1
C1 Capacitor of the electrical circuit
FET GND Control terminal of the electrical circuit
R1 Resistor of the electrical circuit
R2 Resistor of the electrical circuit
R3 Heating means R7 Resistor of the electrical circuit1
R9 Resistor of the electrical circuit
11 Voltage source
12 Wire
13 Sample plate
14 Temperature-regulating block
15 Light-emitting diode
16 Photodiode
17 Acrylic glass plate
18 Double-sided adhesive films
19 Acrylic glass plate
20 Thin film (bottom)
21 Thin film (top)

The invention claimed is:

1. A device for amplifying nucleic acids in a reaction volume comprising:
   a reaction vessel to receive the reaction volume,
   at least one heating element to heat the reaction volume using electrical energy, the at least one heating element comprising a continuous wire at least partially suspended within the reaction vessel, the continuous wire to contact and to be at least partially surrounded by the reaction volume, and
   an electrical circuit configured to transfer the electrical energy into the device via the continuous wire, the electrical energy delivered as electrical pulses applied to the continuous wire and configured to cause heat pulses in the reaction volume,
   wherein the heat pulses cause a localized heating-up zone within the reaction volume, and
   wherein the device is configured such that electrical power consumption of the device during a polymerase chain reaction does not exceed 50 Watt at any point in time.

2. The device of claim 1, wherein the device further comprises an electricity storage that keeps available electrical energy greater than 0.1 J/mL.

3. A device for amplifying nucleic acids in a reaction volume comprising:
   a reaction vessel to receive the reaction volume,
   at least one heating element that runs through and is disposed in the reaction vessel to heat the reaction volume using electrical energy, the at least one heating element comprising a resistive element suspended within the reaction vessel, the at least one heating element to contact and to be at least partially surrounded by the reaction volume, and
   an electrical circuit configured to transfer the electrical energy into the device via electrical pulses applied to the at least one heating element configured to cause heat pulses in the reaction volume, wherein the heat pulses are configured to cause a localized heating-up zone within the reaction volume and wherein the device is configured such that a ratio between electrical power consumption of the device during a polymerase chain reaction and a capacity of the reaction vessel does not exceed 1 Watt per millilitre at any point in time.

4. The device of claim 1, wherein the at least one heating element is conjugated to oligonucleotides, wherein the at least one heating element comprises a heating resistor.

5. The device of claim 1, wherein at least a portion of the at least one heating element is in direct contact with the reaction volume in the reaction vessel, wherein the electrical circuit is configured to cause the heat pulses and, in response, cause the localized heating-up zone within the reaction volume via the application of the electrical pulses such that a global temperature of the reaction volume remains within a threshold of a constant temperature.

6. The device of claim 1, the device comprising a plurality of reaction vessels that are separate from one another, each of the plurality of reaction vessels to receive a separate reaction volume, wherein the reaction vessel is among the plurality of reaction vessels and the at least one heating element comprises a conductive wire, electrical conductor, or a film that is at least partially suspended within each of the plurality of reaction vessels.

7. The device of claim 1, wherein the at least one heating element comprises a conductive wire or conductor disposed within the reaction vessel, the electrical circuit comprising:
   a power source selectively connectable to the at least one heating element; and
   a switch connected to the power source and the at least one heating element to selectively connect the power source to the at least one heating element to generate the electrical pulses applied to the at least one heating element, wherein a volume ratio of the localized heating-up zone to a remaining portion of the reaction volume at an end of a denaturation step of the polymerase chain reaction is less than 10 percent.

8. The device of claim 3, further comprising a plurality of primers fixed on the at least one heating element, wherein a portion of the at least one heating element is in direct contact with the reaction volume, and wherein the electrical circuit is configured to cause the heat pulses and, in response, cause the localized heating-up zone within the reaction volume via the application of the electrical pulses such that a global temperature of the reaction volume increases to below a temperature that causes denaturing of the nucleic acids in the reaction volume.

9. The device of claim 3, further comprising a Universal Serial Bus (USB) connector configured to receive the electrical energy from an external power source and provide the electrical energy to the electrical circuit.

10. The device of claim 3, wherein the electrical circuit is to generate electrical pulses to apply electrical current to the at least one heating element, the electrical circuit comprising:
    a power source selectively connectable to the at least one heating element; and
    a switch connected to the power source and the at least one heating element to selectively connect the power source to the at least one heating element.

11. The device of claim 3, wherein the at least one heating element comprises a heating resistor.

12. The device of claim 3, wherein the at least one heating element comprises a Peltier element.

* * * * *